(12) United States Patent
Sedelmeier

(10) Patent No.: US 8,338,620 B2
(45) Date of Patent: Dec. 25, 2012

(54) METHODS FOR THE PRODUCTION OF C-8 LACTAM LACTONE COMPOUNDS

(75) Inventor: Gottfried Sedelmeier, Schallstadt (DE)

(73) Assignee: Novartis AG, Basel (CH)

( * ) Notice: Subject to any disclaimer, the term of this patent is extended or adjusted under 35 U.S.C. 154(b) by 404 days.

(21) Appl. No.: 12/594,414

(22) PCT Filed: Apr. 1, 2008

(86) PCT No.: PCT/EP2008/053891
§ 371 (c)(1),
(2), (4) Date: Oct. 2, 2009

(87) PCT Pub. No.: WO2008/119804
PCT Pub. Date: Oct. 9, 2008

(65) Prior Publication Data
US 2010/0130749 A1    May 27, 2010

(30) Foreign Application Priority Data

Apr. 3, 2007 (EP) ..................................... 07105572

(51) Int. Cl.
*C07D 207/26* (2006.01)
*C07D 405/04* (2006.01)
*C07C 205/44* (2006.01)
*C07C 205/16* (2006.01)
*C07C 205/29* (2006.01)

(52) U.S. Cl. ......... 548/543; 548/517; 548/530; 568/947
(58) Field of Classification Search .................. 548/517, 548/530, 543; 568/947
See application file for complete search history.

(56) References Cited

U.S. PATENT DOCUMENTS

| | | | | |
|---|---|---|---|---|
| 4,219,660 | A * | 8/1980 | Wehrli | 560/20 |
| 5,559,111 | A | 9/1996 | Goeschke et al. | 514/227.5 |
| 5,606,078 | A | 2/1997 | Goeschke et al. | 549/321 |
| 5,627,182 | A | 5/1997 | Goeschke et al. | 514/237 |
| 5,646,143 | A | 7/1997 | Goeschke et al. | 514/233.8 |
| 5,654,445 | A | 8/1997 | Goeschke et al. | 549/321 |
| 5,659,065 | A | 8/1997 | Goeschke et al. | 560/28 |
| 5,705,658 | A | 1/1998 | Goeschke et al. | 549/321 |
| 7,772,405 | B2 * | 8/2010 | Sedelmeier et al. | 548/517 |

FOREIGN PATENT DOCUMENTS

EP    0 678 503    10/1995
WO    WO 2007/045420    4/2007

OTHER PUBLICATIONS

Kim et al. Synlett 2000, 8, 1151-1153.*
Bergel'son et al. Izvestiya Akademii Nauk SSR, Seriya Khimicheskaya 1964, 8, 1453-56.*
Bergel'son et al. Izvestiya Akademii Nauk SSR, Seriya Khimicheskaya 1964, 8, (Abstract provided).*
Paquette et al. J. Org. Chem. 2003, 68(16), 6097-6107.*
Andrey et al., the use of n-alkyl-2,2'-bipyrrolidine derivatives as organocatalysts for the asymmetric michael addition of ketones and aldehydes to nitroolefins, Advanced Sythesis & Catalysis, 346(9+10), pp. 1147-1168 (2004).
Barluenga et al., "Communications to the Editor", J. Am. Chem. Soc., 121, pp. 4516-4517 (1999).
Haug et al., Synthesis of a gin-phe hydroxy-ethylene dipeptide isostere, Organic Letters, vol. 6, No. 25, pp. 4783-4786 (2004).
Hayashi et al., "Diphenylprolinol silyl ethers as efficient organocatalysts for the asymmetric michael reaction of aldehydes and nitroalkenes", Angew. Chem. Int. 44, pp. 4212-4215 (2005).
Hurd et al., "Ring-chin tautomerism of hydroxy aldehydes", Journal of the American Chemical society, vol. 74, pp. 5324-5329 (1952).
Ito et al, "Trimethylchlorosilane induced ring opening of 2-alkyloxazolidines to enamine derivatives" vol. 26, No. 43, pp. 5303-5306 (195).
Melchiorre et al., "Direct enantioselective michael addition of aldehydes to vinyl ketones catalyzed by chiral amines", JOC Article (2003).
Mitchell et al. A homo-proline tetrazole as an improved organocatalyst for the asymmetric michael addition of carbonyl compounds to nitro-olefins, SYNLETT 4, pp. 611-614 (2004).
Schlinck, Julius, "Pyrrolidine", J. Chem. Soc., Berichte der Deutschen Chemischen Gesellschaft 32, pp. 947-958 (1899).
Shechter et al., "Addition reactions of nitroalkanes with acrolein and methyl vinyl ketone. Selective reduction of nitrocarbonyl compounds to nitrocarbinols", Journal of the American Chemical Society 74, pp. 3664-3668 (1952).
(1952).Zhi,et al., Synthesis of substituted 6-anilinouracils and their inhibition of DNA polymerase IIIC and gram-positive bacterial growth, J. Med. Chem., 46, 2731-2739 (2003).
Registry, ACS, STN on the Web, pp. 1-4, Nov. 16, 1984.
Schlinck, Julius, "Pyrrolidine", J. Chem. Soc., Abstr. 76, I, pp. 539-541, Jan. 1, 1899, downloaded Jun. 5, 2012, http://pubs.rsc.org.

* cited by examiner

*Primary Examiner* — Jason M Nolan
(74) *Attorney, Agent, or Firm* — Daniel Woods

(57) ABSTRACT

The invention related to a novel process, novel process steps and novel intermediates useful in the synthesis of pharmaceutically active compounds, especially renin inhibitors, such as Aliskiren, the invention relates to a process for the manufacture of a compound of the formula I,

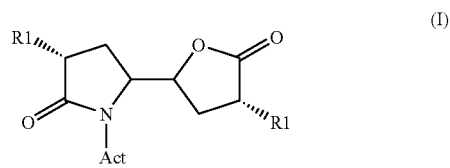

or a salt thereof, wherein R1 as well as Act are as defined in the specification, and processes of manufacturing this compound as well as intermediates in this process.

39 Claims, No Drawings

METHODS FOR THE PRODUCTION OF C-8 LACTAM LACTONE COMPOUNDS

This application is a National Stage Application, filed under 35 USC §371 of Application Number PCT/EP2008/053891, filed Apr. 1, 2008, the contents of which are incorporated herein in their entirety.

FIELD OF THE INVENTION

The present invention relates to novel methods to prepare C-8 lactam lactone compounds. Moreover, the present invention relates to novel intermediates obtained and employed in these methods.

These C-8 lactam lactone compounds are more specifically 5-(5-oxo-tetrahydro-furan-2-yl)pyrrolidin-2-one compounds according to formula (I) as shown below. Such compounds are key intermediates in the preparation of renin inhibitors, in particular 2(S),4(S),5(S),7(S)-2,7-dialkyl-4-hydroxy-5-amino-8-aryl-octanoyl amide derivatives, or pharmaceutically acceptable salts thereof. Therefore, the present invention is also directed to useful intermediates in the preparation of these renin inhibitors as well as methods for preparing these renin inhibitors and its intermediates.

BACKGROUND OF THE INVENTION

Renin passes from the kidneys into the blood where it affects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

With compounds such as (with INN name) aliskiren ((2S,4S,5S,7S)-5-amino-N-(2-carbamo-yl-2-methylpropyl)-4-hydroxy-2-isopropyl-7-[4-methoxy-3-(3-methoxypropoxy)benzyl]-8-methylnonanamide), a new antihypertensive has been developed which interferes with the renin-angiotensin system at the beginning of angiotensin II biosynthesis.

As the compound comprises 4 chiral carbon atoms, the synthesis of the enantiomerically pure compound is quite demanding. Therefore, amended routes of synthesis that allow for more convenient synthesis of this sophisticated type of molecules are welcome.

Such 2(S),4(S),5(S),7(S)-2,7-dialkyl-4-hydroxy-5-amino-8-aryl-octanoyl amide derivatives are any of those having renin inhibitory activity and, therefore, pharmaceutical utility and include, e.g., those disclosed in U.S. Pat. No. 5,559,111. So far, various methods of preparing 2(S),4(S),5(S),7(S)-2,7-dialkyl-4-hydroxy-5-amino-8-aryl-octanoyl amide derivatives are described in the literature.

In EP-A-0678 503, δ-amino-γ-hydroxy-ω-aryl-alkanecarboxamides are described, in particular in the claims and Examples, which exhibit renin-inhibiting properties and could be used as antihypertensive agents in pharmaceutical preparations.

In WO 02/02508, a multistep manufacturing process to obtain δ-amino-γ-hydroxy-ω-aryl-alkanecarboxamides is described, in particular in the claims and Examples, in which the central intermediate is a 2,7-dialkyl-8-aryl-4-octenic acid or a 2,7-dialkyl-8-aryl-4-octenic acid ester. The double bond of this intermediate is simultaneously halogenated in the 4/5 position and hydroxylated in the 4-position via (under) halolactonisation conditions. The halolactone is converted to a hydroxy lactone and then the hydroxy group is converted to a leaving group, the leaving group is substituted with azide, the lactone amidated and then the azide is converted into the amine group.

Further processes for the preparation of intermediates to manufacture δ-amino-γ-hydroxy-ω-aryl-alkanecarboxamides are described in WO02/092828 pertaining to the preparation of 2-alkyl-5-halogenpent-4-ene carboxylic esters, in particular in the claims and Examples, WO 2001/009079 pertaining to the preparation of 2-alkyl-5-halogenpent-4-ene carboxylic acids, in particular in the claims and Examples, WO 02/08172 pertaining to the preparation of 2,7-dialkyl-4-hydroxy-5-amino-8-aryloctanoyl amides, in particular in the claims and Examples, WO 02/02500 pertaining to 2-alkyl-3-phenylpropionic acids, in particular in the claims and Examples, and WO02/024878 pertaining to 2-alkyl-3-phenylpropanols in particular in the claims and Examples.

In EP-A-1215201 an alternative route to obtain δ-amino-γ-hydroxy-ω-aryl-alkanecarboxamides is disclosed, in particular in the claims and Examples. In WO2006/131304 yet an alternative route to obtain δamino-γ-hydroxy-ω-aryl-alkanecarboxamides is disclosed using a pyrrolidine intermediate, in particular in the claims and Examples.

The use of C-8 lactam lactone compounds and more specifically 5-(5-oxo-tetrahydro-furan-2-yl)pyrrolidin-2-one compounds according to formula (I) as shown below, has been first described in WO2007/045420, in particular in the claims and Examples. The C-8 lactam lactone compounds are prepared using auxiliaries, such as the Evans auxiliary and azide chemistry to introduce the nitrogen atom.

Although the existing processes may lead to the desired renin inhibitors, in particular the 2(S),4(S),5(S),7(S)-2,7-dialkyl-4-hydroxy-5-amino-8-aryl-octanoyl amide derivatives, there exists a need to provide an alternative synthetic route to these 2(S),4(S),5(S),7(S)-2,7-dialkyl-4-hydroxy-5-amino-8-aryl-octanoyl amide derivatives to ensure its manufacture in a simple and efficient manner.

SUMMARY OF THE INVENTION

Surprisingly, it has now been found that C-8 lactam lactone compounds, in particular, a 5-(5-oxo-tetrahydro-furan-2-yl) pyrrolidin-2-one, and thus, renin inhibitors, in particular 2(S),4(S),5(S),7(S)-2,7-dialkyl-4-hydroxy-5-amino-8-aryl-octanoyl amide derivatives, are obtainable in high diastereomeric and enantiomeric purity and in an economic manner using a novel approach by utilizing organocatalytic Michael and Henry reactions. In particular it was found that by using theses approaches, chiral intermediates can be prepared in a simple manner with the possibility to conduct the steps in a one-pot fashion or in a continuous flow manner, and at the same time avoiding stoichiometric amounts of chirality-inducing agents, as well as to use inexpensive starting materials. In addition no dangerous azide chemistry is necessary to introduce the nitrogen atom. The important intermediates of these approaches bear unprotected or protected hydroxyl functions which makes the processes much less sensitive to racemization or epimerization during e.g. base promoted reactions. Overall the present invention, thus, simplifies the method of preparing such C-8 lactam lactone compounds and consequently, renin inhibitors, in particular 2(S),4(S),5(S),7(S)-2,7-dialkyl-4-hydroxy-5-amino-8-aryl-octanoyl amide derivatives. As an additional advantage, at least parts of the synthetic route can be performed in a continuous flow manner, thus, rendering the process attractive for commercial applications.

DETAILED DESCRIPTION OF THE INVENTION

The present invention provides methods to obtain a C-8 lactam lactone compound of formula (I)

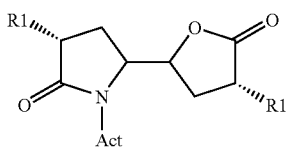

(I)

wherein each $R^1$ is independently of one another hydrogen; $C_{1-7}$alkyl, $C_{3-8}$cycloalkyl or benzyl, in particular both R1 are branched $C_{3-6}$alkyl such as isopropyl; and Act is an activating group selected from an amino protecting group, in particular one that together with N forms a carbamate; or a salt thereof;

using as the key steps organocatalytic Michael and Henry reactions.

In a preferred embodiment, both $R^1$ are $C_{1-7}$alkyl, preferably $C_{2-6}$alkyl, such as methyl, ethyl, n-propyl, isopropyl, isobutyl, or n-butyl; $C_{3-8}$cycloalkyl such as cyclohexyl; or benzyl. Most preferably both $R^1$ are $C_{1-7}$alkyl, in particular branched $C_{3-6}$alkyl, such as isopropyl. In another embodiment, one or both of the $R^1$ are hydrogen.

In a preferred embodiment, Act is an N-protecting group, for example, an amino protecting group which is conventionally used in peptide chemistry (cf.: "Protective groups in Organic Synthesis", $5^{th}$. Ed. T. W. Greene & P. G. M. Wuts, in particular in the relevant chapters thereof, especially in the chemistry of protecting pyrrolidines. In the following the terminology "Act" is maintained throughout the synthesis sequence for sake of consistency. It is appreciated that "Act" serves as an activating group when present on the lactam nitrogen and that after lactam opening the Act group is a protecting group.

Preferred protecting groups comprise, for example, (i) $C_1$-$C_4$-alkyl that is mono-, di- or trisubstituted by phenyl, such as benzyl, (or) benzhydryl or trityl, wherein the phenyl ring is unsubstituted or substituted by one or more, e.g. two or three, residues e.g. those selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; phenyl-C1-C2-alkoxycarbonyl; and allyl or cinnamyl. Especially preferred are benzyloxycarbonyl (Cbz), 9-fluorenylmethyloxycarbonyl (Fmoc), benzyloxymethyl (BOM), pivaloyl-oxy-methyl (POM), trichloroethxoycarbonyl (Troc), 1-adamantyloxycarbonxyl (Adoc), but can also be benzyl, cumyl, benzhydryl, trityl, allyl, $C_{1-10}$ alkenyloxy carbonyl, such as alloc (allyloxycarbonyl). The protecting group can also be silyl, like trialklysilyl, especially trimethylsilyl, tert.-butyl-dimethylsilyl, triethylsilyl, triisopropylsilyl, trimethylsilyethoxymethyl (SEM), and can also be substituted sulfonyl or substituted sulfenyl.

Examples for Act include $C_{1-10}$ alkenyloxy carbonyl, $C_{8-10}$aryl-$C_{1-6}$alkyl, and $C_{1-6}$alkyl-carbonyl, $C_{8-10}$aryl-carbonyl, $C_{1-6}$alkoxy-carbonyl, and $C_{8-10}$aryl-$C_{1-6}$alkoxycarbonyl. In a preferred embodiment, Act is $C_{8-10}$aryl-$C_{1-6}$alkoxycarbonyl, $C_{1-6}$alkoxy-carbonyl, allyloxycarbonyl or $C_{6-10}$aryl-$C_{1-6}$alkyl such as benzyl, t-butoxycarbonyl or benzyloxycarbonyl. In a preferred embodiment, Act is t-butoxy- or benzyloxycarbonyl.

Preferably, the compound according to the formula (I) has the following stereochemistry:

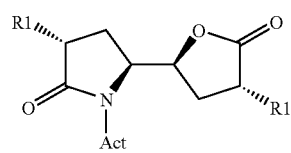

Most preferably, the compound of formula (I) has the following structure:

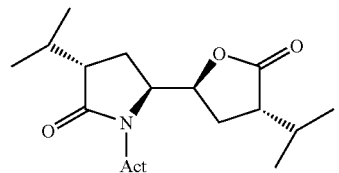

A compound of the formula (I) may be used, inter alia, for the synthesis of pharmaceutically active substances, preferably renin inhibitors such as aliskiren, especially as described in WO2007/045420, in particular in the claims and Examples.

Alternatively, the compound of formula (I) has preferably one of the following structures:

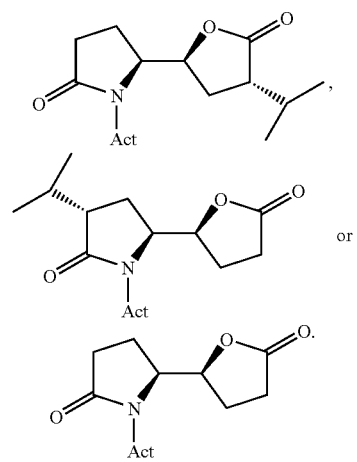

In one embodiment, methods to obtain a C-8 lactam lactone compound of formula (I) provide compounds having one of the following structures:

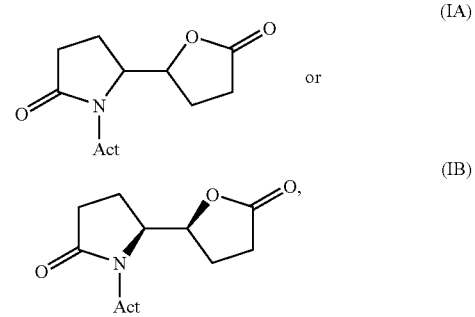

wherein Act is an activating group selected from an amino protecting group, in particular one that together with N forms a carbamate.

In another embodiment, methods to obtain a C-8 lactam lactone compound of formula (I) provide compounds having one of the following structures:

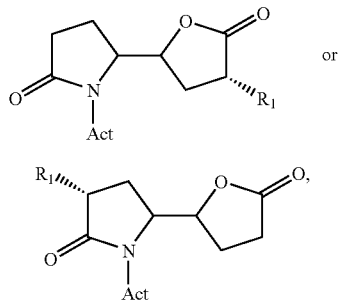

wherein R1 is hydrogen, $C_{1-7}$alkyl, $C_{3-8}$cycloalkyl or benzyl and Act is an activating group selected from an amino protecting group, in particular one that together with N forms a carbamate.

In still another embodiment, methods to obtain a C-8 lactam lactone compound of formula (I) provide compounds having one of the following structures:

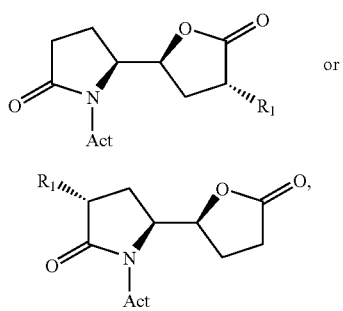

wherein R1 is hydrogen, $C_{1-7}$alkyl, $C_{3-8}$cycloalkyl or benzyl and Act is an activating group selected from an amino protecting group, in particular one that together with N forms a carbamate.

These compounds (IA, IB, IC, ID, IE and IF) are also embodiments of the present invention. They can be transformed to the above dialkyl substituted lactam-lactone by alkylation procedures well known in the art, e.g. in D. H. Rich and B. E. Haug, Organic Letters, &, 4783 (2004), and the references cited therein, wherein the alkylation of the lactone ring is described (in particular see compounds 4 and 3 in Scheme 3), and e.g. in WO2006/024501, wherein the alkylation procedures for lactam rings are disclosed (in particular see compounds (II) and (III) in Scheme 1).

The present inventors have found convenient methods of preparing the key intermediate of the formula (I) as will be described in detail below. Any of the reaction steps either alone or in a suitable combination may be employed to yield the compound of the formula (I). Moreover, any of the following reaction steps either alone or in a suitable combination may be employed in the synthesis of a renin inhibitor, such as aliskiren.

Thus, in one aspect, the present invention relates to a method for preparing a compound of IV),

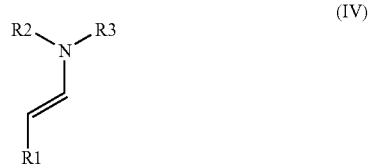

wherein

R1 is hydrogen, $C_{1-7}$alkyl or $C_{3-8}$cycloalkyl;

R2 and R3 together with N form a chiral amine moiety;

or a salt thereof said process comprising subjecting a compound of formula (II)

wherein R1 is as defined for a compound of formula (IV), or a salt thereof, to a chiral amine of formula (III)

wherein R2 and R3 are as defined for a compound of formula (IV), or a salt thereof, to form the enamine moiety. This process step as such, also forms an embodiment of the invention.

Preferred embodiments for $R^1$ can be taken from the definitions for compounds of formula (I). Thus, most preferably, the compound of formula (II) is isovaleryl aldehyde.

Preferably, the amine of formula (III) is a chiral amine, in particular a pyrrolidine derived catalyst suitable for asymmetric Michael addition reactions. Examples of such catalysts include those exemplified in the sketches below.

Organocatalysts for asymmetric Michael - Reactions

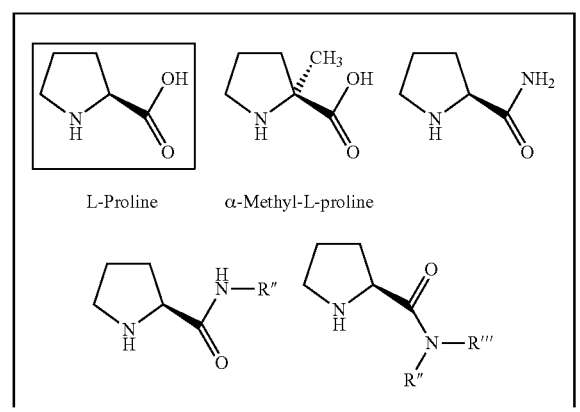

C.F. Barbas III

D.W.C MacMillan

S. Ley

S. Ley

R = Me, Ph
S. Ley

Sedelmeier

Sedelmeier

Berkessel

K. Jorgensen

C. Palomo

C. Tomasini

Tsogoeva

D. J. Dixon

A. Alexakis

K. Jorgensen

R″ = alkyl, cycloalkyl, benzyl, phenyl
R‴ = hydrogen, alkyl, cycloalkyl, benzyl, phenyl L-Proline Wei Wang R′ = natural amino acid side chain L-Alanine, etc.
A. Cordova C. Palomo Yong-M. Liang D.W.C. MacMillan Jin-Pei Cheng
K. Jorgensen S. Tsogoeva Sedelmeier Sedelmeier -continued

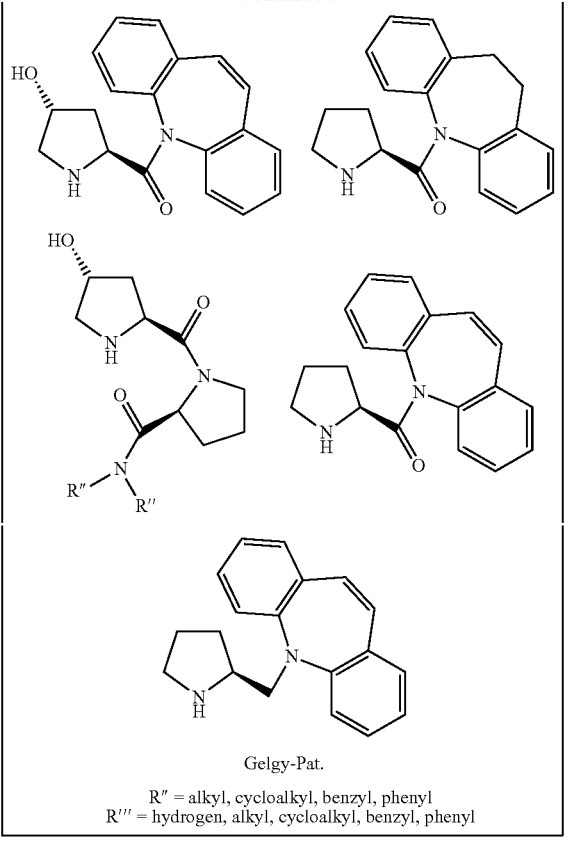

Gelgy-Pat.

R″ = alkyl, cycloalkyl, benzyl, phenyl
R‴ = hydrogen, alkyl, cycloalkyl, benzyl, phenyl These catalysts can be prepared or obtained according to or in analogy to the literature references given below for the organocatalytic nitro-Michael addition including the references cited therein.

For the enamine formation, reference can be made to general methods well known to the person skilled in the art. In particular, the procedures outlined in the reviews and textbook shown below can be adopted:
1.) P. W. Hickmott, Tetrahedron, 38, 1975-2050
2.) P. W. Hickmott, Tetrahedron, 38, 3363-3446
3.) Organikum, 20$^{th}$ ed., Wiley VCH, p. 431.

Thus, a compound of the formula (IV)

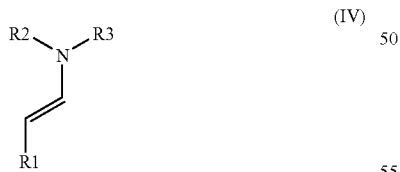

(IV)

wherein
R1 is hydrogen, $C_{1-7}$alkyl, such as $C_{2-7}$alkyl, $C_{3-8}$cycloalkyl or benzyl, in particular $C_{1-7}$alkyl, such as $C_{2-7}$alkyl, $C_{3-8}$cycloalkyl or benzyl;
R2 and R3 together with N form a chiral amine moiety;
or a salt thereof, is a valuable intermediate of the process of preparing renin inhibitors such as aliskiren, in an efficient manner. Therefore such compounds also form an embodiment of the invention.

The definitions for R1, R2 and R3, including the preferred ones, are as defined for compounds of formulae (I) and (III), respectively. Thus, R1 is preferably isopropyl. Preferably the compound of formula (IV) has a structure according to formula (IVa),

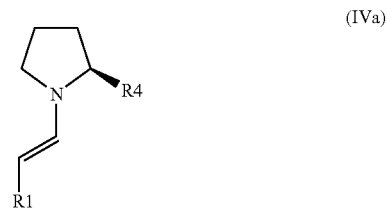

(IVa)

wherein
R4 is carboxy, amido, N (mono- or di-unsubstituted or substituted $C_{2-7}$alkyl) amido, unsubstituted or substituted $C_{1-7}$alkyl or tetrazolyl; or a salt thereof.

Particularly, it is preferred that the compound of formula (IV) has a structure according to (IVb)

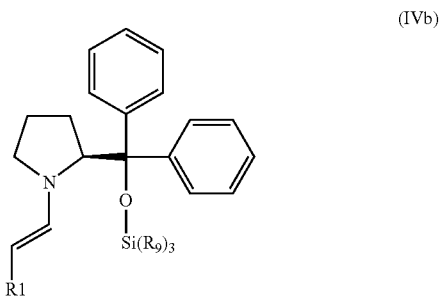

(IVb)

wherein R9 is independently of one another $C_{1-9}$alkyl, such as methyl, ethyl, n-propyl, isopropyl, n-butyl, isobutyl or tert-butyl, or phenyl, preferred is that at least one of the R9 is larger than methyl, such as tert-butyl.

The enamine of formula (IV) can be isolated or formed in situ and be directly reacted on in the organocatalytic nitro-Michael addition reaction. Preferably, the enamine is formed in situ without isolation.

Thus, the present invention also relates as a further step or as an individual to a process for preparing a compound of formula (V),

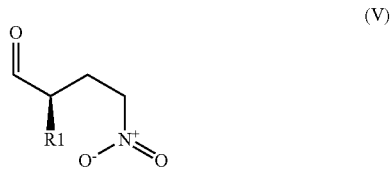

(V)

wherein R1 is as defined for a compound of formula (I), or a salt thereof, said process comprising an organocatalytic nitro-Michael addition reaction of nitroethylene or a precursor thereof with a compound of formula (IV) as defined above. Preferably, this reaction takes place by directly reacting the compounds of formulae (II) and (III) as defined above with the nitroethylene or the precursor thereof without isolating the enamine of formula (IV).

The definitions for R1, R2 and R3, including the preferred ones, are as defined for compounds of formulae (I) and (III), respectively.

It is preferred that the nitroethylene is prepared in situ so that a precursor of nitroethylene is added in the organocatalytic nitro-Michael addition reaction. Typically, the precursor of nitroethylene has a structure of formula (XII)

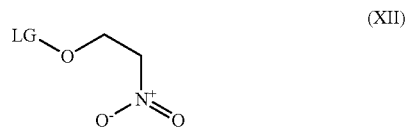

(XII)

wherein —O-LG is a leaving group that is eliminated under the reaction conditions to reveal the nitroethylene. Typical examples for LG are $C_{1-7}$alkylcarbonyl, such as methylcarbonyl, arylcarbonyl, such as phenylcarbonyl, phthaloyl, or $C_{1-7}$alkyl- or arylsulfonyl, such as methansulfonyl and toluolsulfonyl. The precursor is particularly preferably 2-nitroethyl benzoate. The precursors of formula (XII) can be prepared as known in the art, e.g. by esterification of the respective acid or acid chloride with 2-nitroethanol. Procedures are described e.g. in J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999; in particular in the relevant chapters thereof.

Methods of eliminating —O-LG depend on the exact nature of the LG and are also well documented in the art, e.g. in the references mentioned above. For example, if LG is $C_{1-7}$alkylcarbonyl or arylcarbonyl, then it is appropriate to conduct the organocatalytic nitroethylene Michael addition reaction under conditions that eliminate the ester moiety, such as basic conditions, using in particular mild bases such as organic bases, in particular N-containing bases such as N-methyl morpholine or N-ethyl morpholine.

The nitroethylene and the chiral enamine of Formula (IV) react with each other in a stereoselective manner which is driven either by "steric shielding" or by "electronic shielding" due to the chirality of the enamine. The stereochemical outcome of the reaction depends on the chirality of the chiral amine of formula (III), the organo catalyst, (R) or (S) and the corresponding "steric- or electronic shielding".

The reaction conditions for the organocatalytic nitro-Michael addition reaction are well documented in the literature and conditions and catalysts as outlined in the following literature procedures can be adopted:

Some Literature for Organocatalytic Nitro-Michael Additions

1.) A. Alexakis et al., Org. Lett. Vol. 8 (12) 2559 (2006)
2.) S. Ley et al., Synlett, 611 (4), 2005)
3.) S. Ley et al., Org. Biomol. Chem., 3, 84 (2005)
4.) D. Enders et al., Nature, Vol. 441, 861 (2006) and lit. cit.
5.) Y. Hayashi et al., Angew. Chem., Int. Ed. 44, 4212 (2005)
6.) C. F. Barbas et al., J.A.C.S., 128, 4966 (2006)
7.) C. Palomo et al., Angew. Chem., Int. Ed., 45, 5984 (2006)
8.) S. B. Tsogoeva et al., Eur. J. Org. Chem., 4995 (2005)
9.) S. B. Tsogoeva et al., Chem. Commun., 1451 (2006)
10.) A. Alexakis et al., Adv. Synth. Catal., 346, 1147 (2004)
11.) J. P. Cheng et al., Angew. Chem., Int. Ed., 45, 3093 (2006)
12.) N. N. Joshi et al., ARKIVOC, (2002), 167-196; review: enantiosel. Michael addition
13.) M. Gaunt et al., Drug Discov. Today, 12, 8-27 (2007); new organocatalysis review
14.) R. J. Flintoft et al., THL, 40, 4485 (1999); Addition of nitroethylene to ester Li-enolates When forming the compound of formula (V), it is possible that the chiral amine of formula (III) is recycled and can be used again in the reaction with the aldehyde of formula (II). This makes the manufacturing method very economic in that the catalyst can be used in a catalytic amount in contrast to a stoichiometric amount as in the case of using chiral auxiliaries. A preferred amount of the catalyst ranges from 0.5 to 20 mol %, such as 1 to 15 mol %, in particular 5 to 10 mol %. The organocatalysis cycle is illustrated in Scheme I.

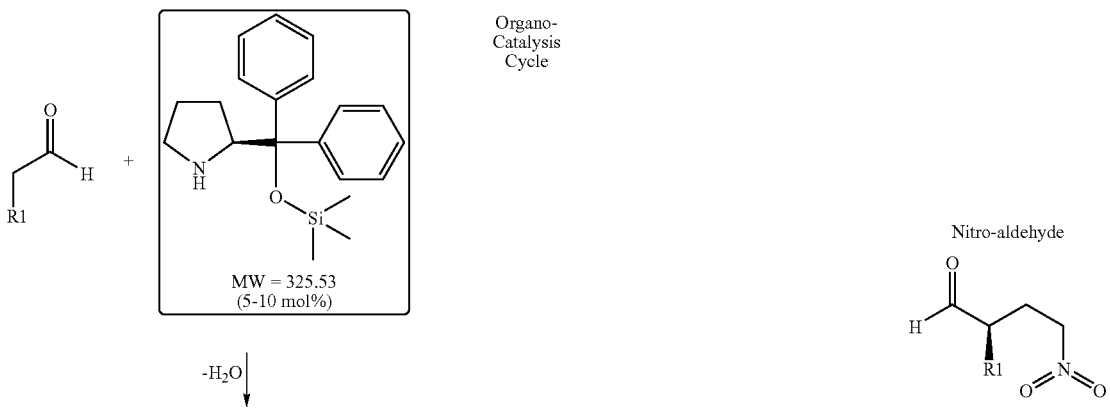

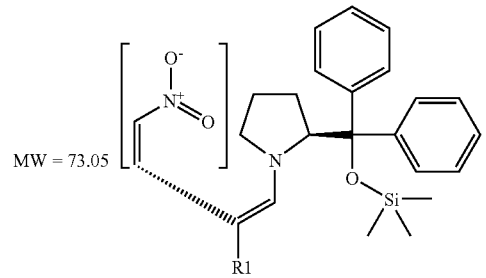
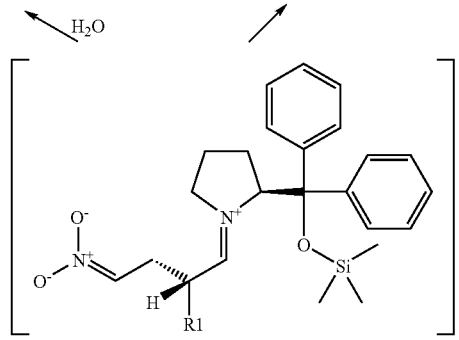
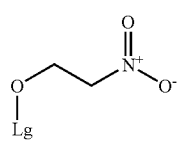

Lg = leaving group

As a particular advantage of this approach, the above reaction cycle can be conducted with an appropriate organo catalyst in a continuous flow manner. With such a continuous flow mode it is possible to scale up the process in an economic fashion. For further detail concerning a continuous flow reaction, reference is made e.g. to Baxendale and Ley, Chem. Comm., 4835 (2006) and the literature cited therein.

Thus, a compound of the formula (V)

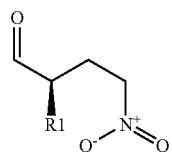
(V)

wherein
R1 is hydrogen, $C_{1-7}$alkyl, such as $C_{2-7}$alkyl, $C_{3-8}$cycloalkyl or benzyl, in particular $C_{1-7}$alkyl, such as $C_{2-7}$alkyl, $C_{3-8}$cycloalkyl or benzyl;
or a salt thereof, is a valuable intermediate of the process of preparing renin inhibitors such as aliskiren, in an efficient manner. Therefore such compounds also form an embodiment of the invention.

The definition for R1, including the preferred ones, are as defined for compounds of formula (I). Thus, R1 is preferably isopropyl.

In a preferred further embodiment of the invention, this synthesis comprises as a further step or as an individual synthesis the process for preparing a compound of formula (VI),

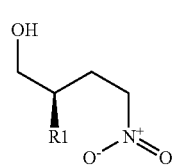
(VI)

wherein R1 is as defined for a compound of formula (I), or a salt thereof, said process comprising the reduction of the aldehyde carbonyl functionality of the compound of formula (V).

The reduction to an alcohol is well known to a person skilled in the art and is described e.g. in Methoden der organischen Chemie" (*Methods of Organic Chemistry*), Houben Weyl, 4th edition, Volume IV/c, Reduction I & II. Georg Thieme Verlag, Stuttgart 1974, in particular in the relevant chapters thereof. The reduction typically takes place in the presence of a suitable reducing agent selected from LSelectride, Lithium trialkoxyaluminium hydrides, for example, lithium tri-tert-butyloxy aluminium hydride, lithium triethylborohydride, tetraalkylammoniumborohydrides and $NaBH_4$ or by addition of a Lewis acid like $CeCl_3$ to the $NaBH_4$. A preferred example of the reagent is $NaBH_4$ due to its selectivity. The reduction takes place preferably in an inert solvent, more preferably in tetrahydrofuran or toluene or in mixtures of THF/water or ethanol/water. The reaction time and the temperature are chosen so as to bring the reaction to completion at a minimum time without the production of unwanted side products. Typically the reaction can be conducted at 0° C. to reflux, preferably 10 to 80° C., more preferably 15 to 40° C., such as 20-25° C., for 1 min to 3 h, preferably 10 min to 2 h, most preferably 20 min to 2 h.

If the reaction is carried out following the conversion to a compound of formula (V), it is possible and preferred that the compound of formula (V) is reduced without isolating it. It is therefore an option to perform the reduction step, preferably together with the aforementioned organocatalytic nitro-Michael addition reaction, in a continuous flow manner. In such a case the reduction is preferably carried out under continuous flow catalytic conditions. For further detail see the literature cited above in connection with the continuous flow reaction.

Thus, a compound of the formula (VI)

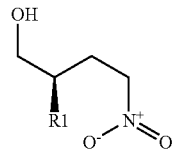
(VI)

wherein

R1 is hydrogen, $C_{1-7}$alkyl, such as $C_{2-7}$alkyl, $C_{3-8}$cycloalkyl or benzyl, in particular $C_{1-7}$alkyl, such as $C_{2-7}$alkyl, $C_{3-8}$cycloalkyl or benzyl;

or a salt thereof, is a valuable intermediate of the process of preparing renin inhibitors such as aliskiren, in an efficient manner. Therefore such compounds also form an embodiment of the invention.

The definition for R1, including the preferred ones, are as defined for compounds of formula (I). Thus, R1 is preferably isopropyl.

The nitroalcohol of formula (VI) is one of the possible starting materials for the nitro-aldol (Henry) reaction which will be described later. The other reagent, the aldehyde of formula (VIII) as described below, can be prepared as shown below or as described in the examples.

If using a compound of formula (VI) as the starting material for the aldehyde, it can be the same compound of formula (VI) (same R1) as the reagent for the nitro-aldol reaction, or different compounds of formula (VI) can be used for the preparation of the aldehyde on the one hand and as the starting material for the nitro-aldol reaction on the other hand.

In a preferred further embodiment of the invention, this synthesis comprises as a further step or as an individual synthesis process for preparing a compound of formula (VII)

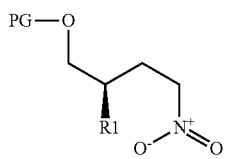
(VII)

wherein R1 is as defined for a compound of formula (I) and PG is a hydroxyl protecting group, or a salt thereof, said process comprising an protecting the hydroxyl functionality of the compound of formula (VI) as defined above with a protecting group.

Typical procedures to protect the hydroxyl functionality can be taken from the literature references cited in the section "General process conditions" below in connection with protecting groups. Preferably, PG is a benzyl group since this group can be removed selectively and conveniently by hydrogenation. Other preferred examples of protecting groups are e.g., p-methoxybenzyl, o,m,p-pyridylmethyl and silyl protecting groups as mentioned in the references cited in the section "General process conditions" below, in particular TMS, TES, TIPS and TBDMS.

Thus, a compound of the formula (VII)

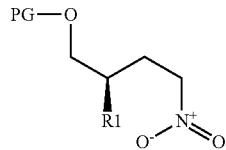
(VII)

wherein R1 is as defined for a compound of formula (I) and PG is a hydroxyl protecting group, or a salt thereof, is a valuable intermediate of the process of preparing renin inhibitors such as aliskiren, in an efficient manner. Therefore such compounds also form an embodiment of the invention.

The definitions for R1 and PG, including the preferred ones, are as defined for compounds of formulae (I) and as described above, respectively. Thus, R1 is preferably isopropyl. PG is preferably benzyl.

In a preferred further embodiment of the invention, this synthesis comprises as a further step or as an individual synthesis the process for preparing a compound of formula (VIII),

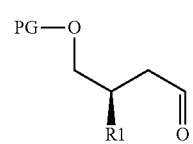
(VIII)

wherein R1 is as defined for a compound of formula (I) and PG is as defined for a compound of formula (VII), or a salt thereof, said process comprising a Nef reaction of the compound of formula (VII) as defined above to convert the nitro functionality to an aldehyde functionality.

The reaction conditions for the Nef reaction are well documented in the literature and conditions as outlined in the following literature procedures can be adopted:
a) P. Ceccherelli, et al., Synth. Commun. 28, 3054 (1998)
b) G. Kabalka, et al., Synth. Commun. 22, 2587 (1992)
c) F. Urpi, et al., THL, 31, 7499 (1990)
d) H. Chikashita et al., Synth. Commun., 17, 677 (1987)
e) R. Ballini, M. Petrini, Tetrahedron, 60, 1017 (2004), review Thus, a compound of the formula (VIII)

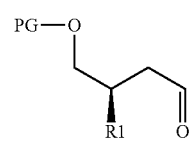
(VIII)

wherein R1 is as defined for a compound of formula (I) and PG is a hydroxyl protecting group, or a salt thereof, is a valuable intermediate of the process of preparing renin inhibitors such as aliskiren, in an efficient manner. Therefore such compounds also form an embodiment of the invention.

The definitions for R1 and PG, including the preferred ones, are as defined for compounds of formulae (I) and as described above, respectively. Thus, R1 is preferably isopropyl. PG is preferably benzyl.

Alternatively, the compound of formula (VIII) can be prepared by using a chloride compound of formula (XIII) and reacting with cyanide to form the corresponding nitrile of formula (XIV) and reducing the nitrile to obtain the aldehyde of formula (VIII).

Thus, in a preferred further embodiment of the invention, this synthesis comprises as a further step or as an individual synthesis the process for preparing a compound of formula (XIV),

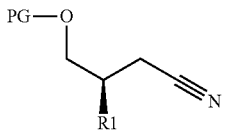
(XIV)

wherein R1 is as defined for a compound of formula (I) and PG is as defined for a compound of formula (VII), or a salt thereof, said process comprising reacting a compound of formula (XIII)

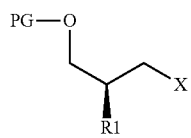
(XIII)

wherein R1 is as defined for a compound of formula (I) and PG is as defined for a compound of formula (VII) and X is a halogen, or a salt thereof, with a source of CN⁻ to convert the chloride functionality to a nitrile functionality.

Compounds of formula (XIII) can be prepared following the procedures as disclosed e.g. in Helv. Chim. Acta, 86, (8) 2848 (2003).

X is a halogen such as chlorine, bromine or iodine, preferably chlorine.

The substitution of a halogen to a nitrile is well known to a person skilled in the art and is described e.g. in Organikum, 20$^{th}$ ed, Wiley VCH, p. 245-247, and literature cited therein. The substitution typically takes place in the presence of a CN⁻ source selected from metal cyanides, for example, NaCN, LiCN, KCN or N(C$_{1-7}$alkyl)$_4$CN. A preferred example of the reagent is NaCN. The reaction takes place preferably in an inert solvent, more preferably in DMSO, DMF, NMP, glyme, diglyme or tetrahydrofuran. The reaction time and the temperature are chosen so as to bring the reaction to completion at a minimum time without the production of unwanted side products. Typically the reaction can be conducted at 0° C. to reflux, preferably 10 to 120° C., more preferably 20 to 100° C., such as 50-90° C., for 1 h to 5 h, preferably 2 min to 3 h, most preferably 3 h.

Thus, a compound of the formula (XIV)

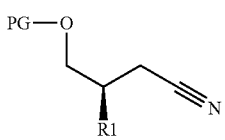
(XIV)

wherein R1 is as defined for a compound of formula (I) and PG is a hydroxyl protecting group, or a salt thereof, is a valuable intermediate of the process of preparing renin inhibitors such as aliskiren, in an efficient manner. Therefore such compounds also form an embodiment of the invention.

The definitions for R1 and PG, including the preferred ones, are as defined for compounds of formulae (I) and as described above, respectively. Thus, R1 is preferably isopropyl. PG is preferably benzyl.

Moreover, in a preferred further embodiment of the invention, this synthesis comprises as a further step or as an individual synthesis the process for preparing a compound of formula (VIII),

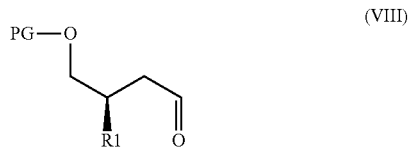
(VIII)

wherein R1 is as defined for a compound of formula (I) and PG is as defined for a compound of formula (VII), or a salt thereof, said process reduction of the nitrile functionality of a compound of formula (XIV) as defined above to convert the nitrile functionality to an aldehyde functionality.

The reduction of a nitrile to an aldehyde is well known to a person skilled in the art and is described e.g. in J. Organic Chemistry, 24, 627 (1959), J. Organic Chemistry, 46, 5250 (1981) and Tetrahedron Letters, 32, 4115 (1991). The reduction typically takes place in the presence of an H⁻ source selected from hydrides, for example, DIBAH. A preferred example of the reagent is DIBAH. The reaction takes place preferably in an inert solvent, more preferably in dichloromethane, hexane, heptane, cyclohexane toluene or tetrahydrofuran or mixtures of these. The reaction time and the temperature are chosen so as to bring the reaction to completion at a minimum time without the production of unwanted side products. Typically the reaction can be conducted at −20° C. to reflux, preferably −10 to 50° C., more preferably −5 to 30° C., such as 0° C., for 30 min to 5 h, preferably 1 min to 3 h, most preferably 2 h.

As mentioned before, the aldehyde of formula (VIII) is a starting material for the nitro-aldol reaction.

Thus, in a preferred further embodiment of the invention, this synthesis comprises as a further step or as an individual synthesis the process for preparing a compound of formula (IX),

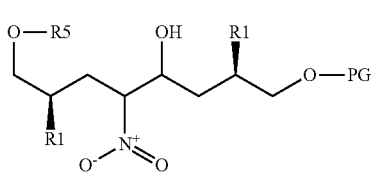
(IX)

wherein both R1's are the same or different from each other and are as defined for a compound of formula (I), R5 is hydrogen or PG, and PG is as defined for a compound of formula (VII), whereby both PG's can be the same or different, or a salt thereof, said process comprising a nitro-aldol (Henry) reaction of the nitro compound of formula (VI) as defined above, when R5 is H, or the O-protected nitro compound of formula (VII) as defined above, when R5 is PG, together with the aldehyde of formula (VIII) as defined above.

Preferably the reagents are the aldehyde of formula (VIII) and the nitro compound of formula (VI) to obtain a compound of formula (IX) wherein R5 is H. Alternatively the reagents are the aldehyde of formula (VIII) and the O-protected nitro compound of formula (VII) to obtain a compound of formula (IX) wherein R5 is PG, whereby both PG's in the compound of formula (IX) are preferably the same so that they can be removed in a single step. Preferably PG is in this case benzyl.

Depending on the nature of the reagents of formulae (VI) or (VII) and (VIII) used, the R1's can be the same or different. Preferably, they are the same and as defined herein, e.g. they are both isopropyl.

The reaction conditions for the nitro-aldol (Henry) reaction are well documented in the literature and conditions and catalysts as outlined in the following literature procedures can be adopted:

Some Literature for Metal Catalytic & Organocatalytic Nitro-Aldol Reactions

1.) F. A. Luzzio, Tetrahedron, 57, 915-945 (2001); general review
2.) N. C. Barua et al., Tetrahedron: Asym. 17, 3315 (2006); general review. asym. Henry
3.) K. Nagasawa et al., Adv. Synth. Catal., 347, 1643 (2005); organocatalytic
4.) H. Hiemstra et al., Ang. Chem., Int. Ed., 45, 929 (2006); organocatalytic
5.) Y. Takemoto et al., Chem. Eur. J., 12, 466 (2006); organocatal. Aza-Henry
6.) H. Maheswara et al., Chem. Commun., 4066 (2006); Cu-II-sparteine catalyst
7.) K. Nagasawa et al., Eur. J. Org. Chem., 2894 (2006); organocatalytic (high syn)
8.) M. Shibasaki et al., Chem. Rev., 102, 2187-2209 (2002); La—Li-BINOL-catalyst
9.) B. Trost et al., Org. Lett., 4, 2621 (2002); Zn-Ligand catalyst
10.) D. Evans et al., J.A.C.S., 125, 12692 (2003); Cu-BOX-Ligand catalyst
11.) C. Palomo et al., Angew. Chem., 117, 3949 (2005); Zn-NME-Ligand catalyst For the enantioselective and diastereoselective nitro-aldol reaction of a compound of formula (VI) or (VII) with a compound of formula (VIII), different catalysts can be used, either organocatalysts or chiral metal ligand complexes, e.g. Shibasaki system, Evans system or Trost system [see cited literature in references 1.), 2.) and 5.)]. As a preferred catalyst the Shibasaki system (see reference 8) or the Nagasawa system (see reference 7) can be employed using literature procedures. In one embodiment, the organocatalyst is a chiral amine, for example sparteine.

The routes to the nitro-aldol reaction can be summarized below in Scheme 2:

Scheme 2: Overview of routes to nitro-aldol reaction

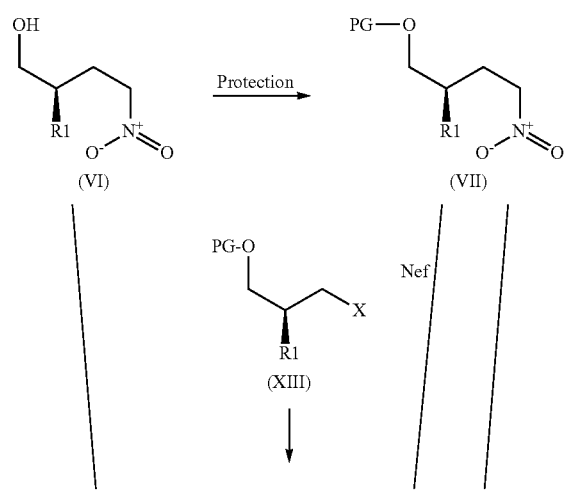

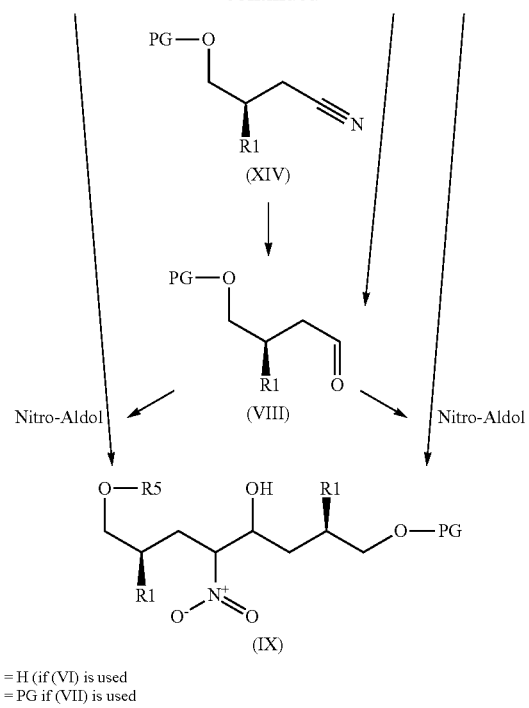

R5 = H (if (VI) is used
R5 = PG if (VII) is used

Thus, a compound of the formula (IX)

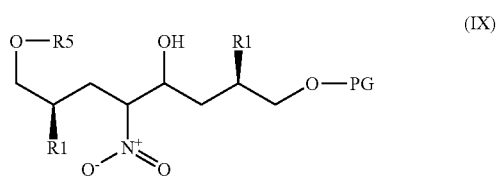

wherein both R1's are the same or different from each other and are hydrogen, $C_{1-7}$alkyl, such as $C_{2-7}$alkyl, $C_{3-8}$cycloalkyl or benzyl, in particular $C_{1-7}$alkyl, such as $C_{2-7}$alkyl, $C_{3-8}$cycloalkyl or benzyl;

R5 is hydrogen or PG;

PG is a hydroxyl protecting group and whereby both PG's can be the same or different;

or a salt thereof, is a valuable intermediate of the process of preparing renin inhibitors such as aliskiren, in an efficient manner. Therefore such compounds also form an embodiment of the invention.

The definitions for R1 and PG, including the preferred ones, are as defined for compounds of formulae (I) and as described above, respectively. Thus, R1 is preferably isopropyl. PG is preferably benzyl. It is also preferred that both R1's are the same. It is also preferred that if both PG's are present they are the same. Most preferably, R5 is hydrogen.

The compounds of formula (IX) have preferably the structure of formula (IXa)

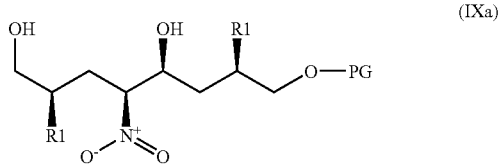

wherein the definitions for R1 and PG, including the preferred ones, are as defined herein. The stereo selectivity at the hydroxyl function can be controlled by using the appropriate catalyst as described in the above literature references.

In a preferred further embodiment of the invention, this synthesis comprises as a further step or as an individual synthesis the process for preparing a compound of formula (X),

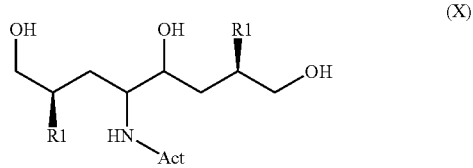

wherein both R1's are the same or different from each other and are as defined for a compound of formula (I), and Act is an activating group selected from an amino protecting group, in particular one that together with N forms a carbamate, or a salt thereof, said process comprising hydrogenation of the nitro functionality of the compound of formula (IX).

Hydrogenation typically takes place in the presence of a catalyst selected from a heterogeneous catalyst or a homogeneous catalyst, such as Wilkinson's catalyst, preferably a heterogeneous catalyst. Examples of the catalyst include Raney nickel, palladium/C, Pd(OH)$_2$ (Perlman's catalyst), nickel boride, platinum metal or platinum metal oxide, rhodium, ruthenium and zinc oxide, more preferably Raney nickel, palladium/C, platinum metal or platinum metal oxide, most preferably palladium/C or Raney nickel. The catalyst is preferably used in an amount of 1 to 20%, more preferably 5 to 10%. The reaction can be conducted at atmospheric or elevated pressure, such as a pressure of 2-10 bar, e.g. 5 bar, more preferably the reaction is conducted at atmospheric pressure. The hydrogenation takes place preferably in an inert solvent, more preferably in tetrahydrofuran or toluene. Also suitable are protic solvents, such as alcohol, e.g. ethanol or methanol, or ethyl acetate. These solvents may be used in the presence of water. The reaction time and the temperature are chosen so as to bring the reaction to completion at a minimum time without the production of unwanted side products. Typically the reaction can be conducted at 0° C. to reflux, preferably 0 to 60° C., such as 0 to 40° C., more preferably 15-30° C., such as room temperature, for 10 min to 12 h, preferably 20 min to 6 h, most preferably 30 min to 4 h, such as 1 to 3 h or 6 to 12 h.

It is preferred from an economic standpoint to use as few steps as possible in the reaction sequence. Therefore, it is preferred that the removal of the protecting group(s) PG is conducted concomitantly. This can be achieved if the protecting group(s) PG are selected from e.g. benzyl groups. Alternatively, the protecting group(s) PG can be removed as a separate step by methods well known in the art and as described herein, in particular the literature references cited in the section "General process conditions" below in connection with protecting groups, to reveal the hydroxyl functionality.

Again, it is preferred from an economic standpoint to use as few steps as possible in the reaction sequence. Therefore, it is preferred that the introduction of the activating group Act is conducted concomitantly. This can be achieved by using the reagent, e.g. as a solvent or co-solvent, in the hydrogenation reaction. This is particularly appropriate if Act is an alkoxy carbonyl group so as to form, together with N, a carbamate, where the corresponding alkoxy carbonyl anhydride, e.g. BOC anhydride, can be present in the hydrogenation reaction either stoichiometrically or in excess. Reaction conditions can be the same as described below.

Alternatively, the group Act can be introduced in a separate step by methods well known in the art and as described herein, in particular the literature references cited in the section "General process conditions" below in connection with protecting groups, to protect the amine functionality. Fore example this conversion proceeds under standard conditions and as described e.g. in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974, in particular in the relevant chapters thereof.

In particular when Act is an alkoxy carbonyl group so as to form, together with N, a carbamate, the reaction is preferably conducted under basic conditions. The base can be used stoichiometrically or catalytically. Suitable bases include organic or inorganic bases, preferably organic bases, more preferably a nitrogen base, yet more preferably a tertiary nitrogen base. Examples of the tertiary nitrogen base include triethylamine, diisopropylethylamine, DBU, TMEDA and trimethylamine. DMAP can be used as a catalyst. The reaction can be conducted in any suitable solvent, preferably a polar solvent such as an ethyl acetate or isopropyl acetate, an ether, such as THF or TBME, an alcohol, such as methanol, ethanol or isopropanol, or a halogenated solvent, more preferably THF, methylene chloride or isopropyl acetate. The reaction time and the temperature are chosen so as to bring the reaction to completion at a minimum time without the production of unwanted side products. Typically the reaction can be conducted at 0° C. to reflux, preferably 0 to 60° C., more preferably 15-50° C., such as 20-45° C., for 10 min to 36 h, preferably 3 h to 24 h, most preferably 6 h to 24 h, such as 12-17 h.

Most preferably, the compound of formula (X) is obtained in a one-pot synthesis from a compound of formula (IX) using hydrogenation in the presence of (Act)$_2$O, such as (Boc)$_2$O.

Thus, a compound of the formula (X)

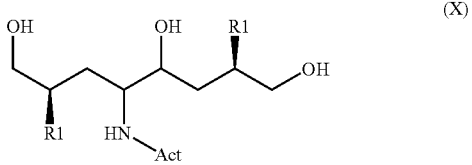

wherein
both R1's are the same or different from each other and are hydrogen, $C_{1-7}$alkyl, such as $C_{2-7}$alkyl, $C_{3-8}$cycloalkyl or benzyl, in particular $C_{1-7}$alkyl, such as $C_{2-7}$alkyl, $C_{3-8}$cycloalkyl or benzyl; and Act is an activating group selected from an amino protecting group, in particular one that together with N forms a carbamate;

or a salt thereof, is a valuable intermediate of the process of preparing renin inhibitors such as aliskiren, in an efficient manner. Therefore such compounds also form an embodiment of the invention.

The definitions for R1 and Act, including the preferred ones, are as defined for compounds of formula (I). Thus, R1 is preferably isopropyl. Act is preferably alkoxy carbonyl, in particular butoxy carbonyl (BOC). It is also preferred that both R1's are the same.

The compounds of formula (X) have preferably the structure of formula (Xa)

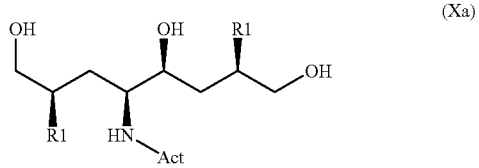

In a preferred further embodiment of the invention, this synthesis comprises as a further step or as an individual synthesis the process for preparing a compound of formula (I),

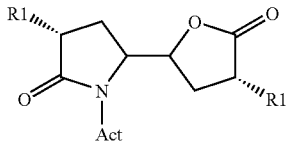

wherein R1 and Act are as defined above, or a salt thereof, said process comprising selective oxidation of the primary alcohols of the compound of formula (X) as defined above to effect double ring closure into the lactone lactam.

The selective oxidation of the primary alcohol preferably takes place under conditions so as to keep the other functionalities on the molecule intact, in particular the secondary alcohol but also the Act group. Selectivity is generally achieved due to the lower reactivity of the secondary alcohol Such a reaction is well known to a person skilled in the art and is described e.g. in S. Ley, Synthesis, 639, (1994) and K. H. Altmann, Tet. Lett., 34, 7721 (1993). Suitable oxidants are mild oxidants that avoid over-oxidation, in particular mild oxidative systems using a catalyst are preferred. Such a system is e.g. N-methyl morpholine N-oxide (oxidant) together with tetrapropyl ammonium perruthenate (TPAP) as the catalyst. It is preferred that the oxidant is used in excess to ensure good conversion rates. The catalyst is typically employed in an amount of 1 to 20 mol %, such as 5 to 10 mol %. Due to the position of the amine and the secondary alcohol in the molecule, spontaneous cyclization to form the lactam and the lactone, respectively, occurs. The cyclization is in equilibrium with the ring opening, so that removal of the water formed during the ring closure is preferred to drive the equilibrium towards the lactone lactam. The removal of water can be achieved by entrapment in a Dean Stark apparatus, if reflux conditions are used, or in general by placing molecular sieves in the reaction mixture.

As an alternative route to the compounds of formula (I) but still using the nitro-aldol approach, the aldehyde compound of formula (VIII) can be reacted with a nitroester followed by hydrogenation and oxidation.

Thus, in a preferred further embodiment of the invention, this synthesis comprises as a further step or as an individual synthesis the process for preparing a compound of formula (XVI),

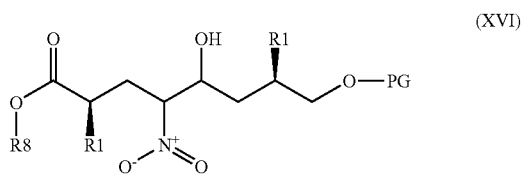

wherein both R1's are the same or different from each other and are as defined for a compound of formula (I), R8 is $C_{1-7}$alkyl, and PG is as defined for a compound of formula (VII), or a salt thereof, said process comprising a nitro-aldol (Henry) reaction of the nitro compound of formula (XV)

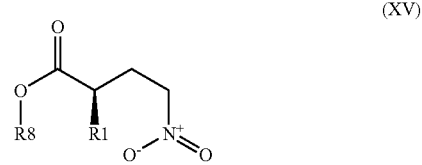

wherein R8 is $C_{1-7}$alkyl, R1 is as defined for a compound of formula (IV) and PG is a hydroxyl protecting group, or a salt thereof, together with the aldehyde of formula (VIII) as defined above.

Compounds of formula (XV) are commercially available or can be prepared by methods known to the person skilled in the art.

Preferably, R8 is $C_{1-4}$alkyl, in particular methyl or ethyl, specifically methyl. R1 is hydrogen, $C_{1-7}$alkyl, $C_{3-8}$cycloalkyl or benzyl, in particular $C_{1-7}$alkyl or hydrogen, in particular hydrogen.

The definitions for R1 and PG in compound of formula (XVI), including the preferred ones, are as defined for compounds of formulae (I) and as described above, respectively. Thus, R1 is preferably isopropyl. PG is preferably benzyl.

The reaction conditions are analogous to the ones provided for the preparation of compounds of formula (IX) as described above.

Thus, a compound of the formula (XVI)

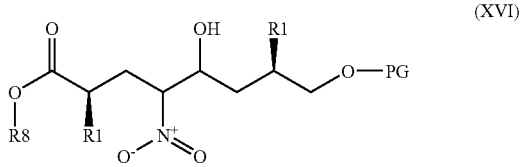

wherein
both R1's are the same or different from each other and are hydrogen, $C_{1-7}$alkyl, $C_{3-8}$cycloalkyl or benzyl, in particular hydrogen or $C_{1-7}$alkyl;
R8 is $C_{1-7}$alkyl;
PG is a hydroxyl protecting group;
or a salt thereof, is a valuable intermediate of the process of preparing renin inhibitors such as aliskiren, in an efficient manner. Therefore such compounds also form an embodiment of the invention.

The definitions for R1, R8 and PG, including the preferred ones, are as defined for compounds of formulae (I) and as described above, respectively. Thus, R1 is preferably hydrogen or isopropyl. PG is preferably benzyl. It is also preferred that both R1's are the same. Alternatively, one is hydrogen and the other is isopropyl. Most preferably, R8 is methyl.

The compounds of formula (XVI) have preferably the structure of formula (XVIa)

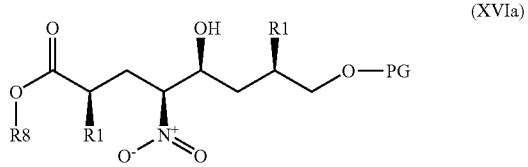

wherein the definitions for R1, R8 and PG, including the preferred ones, are as defined herein. The stereo selectivity at the hydroxyl function can be controlled by using the appropriate catalyst as described in the above literature references.

In a preferred further embodiment of the invention, this synthesis comprises as a further step or as an individual synthesis the process for preparing a compound of formula (XVII),

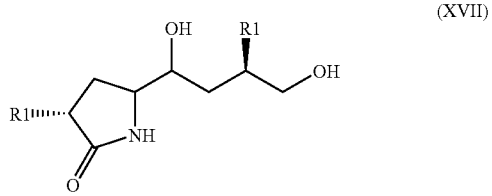

wherein both R1's are the same or different from each other and are as defined for a compound of formula (I), or a salt thereof, said process comprising hydrogenation of the nitro functionality of the compound of formula (XVI) and ring closure to form the lactam, said process, comprising as a concomitant or separate step the removal of the protecting group PG to reveal the hydroxyl functionality.

Upon hydrogenation of the nitro functionality of the compound of formula (XVI) ring closure to form the lactam typically occurs spontaneously. The reaction conditions for the hydrogenation are analogous to the ones provided for the preparation of compounds of formula (X) as described above.

It is preferred from an economic standpoint to use as few steps as possible in the reaction sequence. Therefore, it is preferred that the removal of the protecting group PG in a compound of formula (XVI) is conducted concomitantly. This can be achieved if the protecting group(s) PG are selected from e.g. benzyl groups. Alternatively, if PG is benzyl, the two hydrogenation reactions can be conducted as separate steps. The reaction conditions for the hydrogenation to remove PG=benzyl are analogous to the ones provided for the preparation of compounds of formula (X) as described above. Alternatively, the protecting group PG, in particular if other than benzyl, can be removed as a separate step by methods well known in the art and as described herein, in particular the literature references cited in the section "General process conditions" below in connection with protecting groups, to reveal the hydroxyl functionality.

Thus, a compound of the formula (XVII),

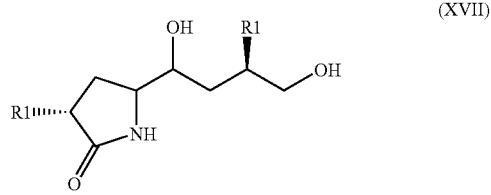

wherein
both R1's are the same or different from each other and are hydrogen, $C_{1-7}$alkyl, such as $C_{2-7}$alkyl, $C_{3-8}$cycloalkyl or benzyl;
or a salt thereof, is a valuable intermediate of the process of preparing renin inhibitors such as aliskiren, in an efficient manner. Therefore such compounds also form an embodiment of the invention.

The definitions for R1, including the preferred ones, are as defined for compounds of formula (I). Thus, R1 is preferably hydrogen or isopropyl. It is also preferred that both R1's are the same or one is hydrogen and the other is isopropyl.

The compounds of formula (XVII) have preferably the structure of formula (XVIIa),

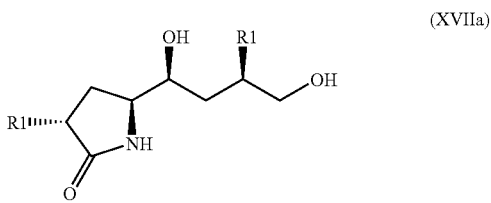

In a preferred further embodiment of the invention, this synthesis comprises as a further step or as an individual synthesis the process for preparing a compound of formula (XVIII),

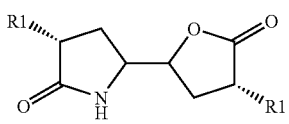

(XVIII)

wherein R1 are as defined above, or a salt thereof, said process comprising selective oxidation of the primary alcohol of the compound of formula (XVII) as defined above to effect ring closure into the lactone lactam.

Alternatively, the compound of formula (XVIII) has preferably one of the following structures:

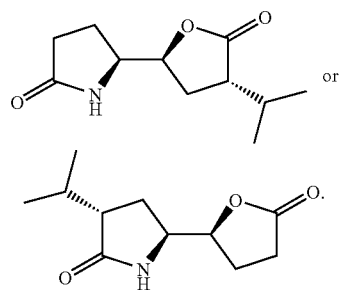

In one embodiment, methods to obtain a C-8 lactam lactone compound of formula (XVIII) provide compounds having one of the following structures:

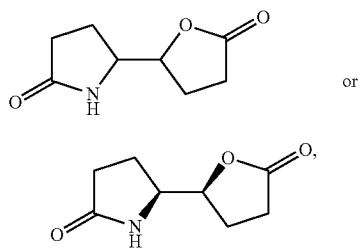

(XVIIIA)

or (XVIIIB)

wherein Act is an activating group selected from an amino protecting group, in particular one that together with N forms a carbamate.

In another embodiment, methods to obtain a C-8 lactam lactone compound of formula (XVIII) provide compounds having one of the following structures:

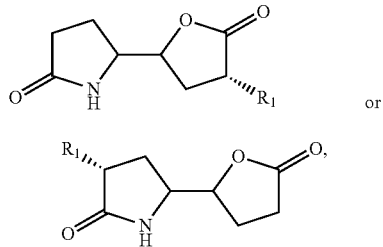

(XVIIIC)

or (XVIIID)

wherein R1 is hydrogen, $C_{1-7}$alkyl, $C_{3-8}$cycloalkyl or benzyl and Act is an activating group selected from an amino protecting group, in particular one that together with N forms a carbamate.

In still another embodiment, methods to obtain a C-8 lactam lactone compound of formula (XVIII) provide compounds having one of the following structures:

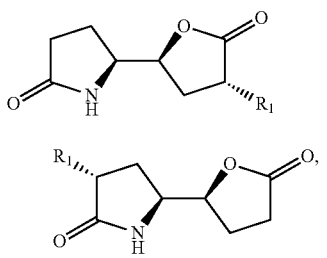

(XVIIIE)

or (XVIIIF)

wherein R1 is hydrogen, $C_{1-7}$alkyl, $C_{3-8}$cycloalkyl or benzyl and Act is an activating group selected from an amino protecting group, in particular one that together with N forms a carbamate.

These compounds (XVIIIA, XVIIIB, XVIIIC, XVIIID, XVIIIE and XVIIIF) are also embodiments of the present invention.

Upon oxidation of the primary alcohol of the compound of formula (XVII) ring closure to form the lactone typically occurs spontaneously. The reaction conditions for the oxidation are analogous to the ones provided for the preparation of compounds of formula (I) as described above. Introduction of the group Act to obtain compounds of the formula (I) can be achieved as known in the art and in particular as described in the preparation of a compound of formula (X), e.g. as described in WO2007/045420, in particular in the claims and Examples.

Each of the above mentioned method steps can be used individually in a method to prepare renin inhibitors such as aliskiren. Preferably the steps are used in combination of one or more, most preferably all, to prepare renin inhibitors such as aliskiren. A lactam lactone of formula (I) can be converted to aliskiren as described, e.g. in WO2007/045420, in particular in the claims and Examples.

In another embodiment, the present invention relates to a process for preparing a compound of formula (XI)

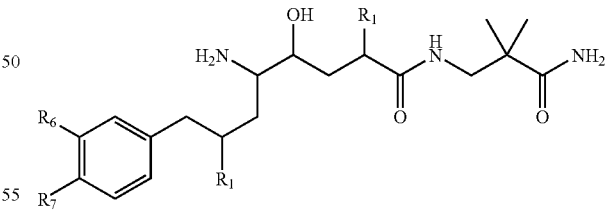

(XI)

wherein R1 is as defined for a compound of formula (I), R6 is halogen, hydroxyl, $C_{1-6}$halogenalkyl, $C_{1-6}$alkoxy-$C_{1-6}$alkyloxy or $C_{1-6}$alkoxy-$C_{1-6}$alkyl; R7 is halogen, hydroxyl, $C_{1-4}$alkyl or $C_{1-4}$alkoxy, or a salt thereof, comprising one or more of the following steps either individually or in any combination:

the manufacture of a compound of the formula IV as defined above, the manufacture of a compound of the formula V as defined above, the manufacture of a compound of the formula VI as defined above, the manufacture of a compound of the formula VII as defined above, the manufacture of a compound of the formula VIII as defined above, the manufacture of a compound of the formula IX as defined above, the manufacture of a compound of the formula X as defined above, and the manufacture of a compound of the formula as defined above.

Most preferably the compound of formula (XI) is aliskiren.

All these different synthesis steps and routes show that with compounds of the formula (VI), (VII) and (VIII) but also (X) highly important new compounds have been found that are central intermediates to a number of possible synthesis routes especially for the synthesis of renin inhibitors such as aliskiren. Therefore, these compounds of the formulae (VI) and (VIII), but also (X) or a salt thereof, as well as their syntheses form very highly preferred embodiments of the invention.

Listed below are definitions of various terms used to describe the novel intermediates and synthesis steps of the present invention. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

Alkyl being a radical or part of a radical is a straight or branch (one or, if desired and possible, more times) carbon chain, and is especially $C_1$-$C_7$-alkyl, such as $C_1$-$C_4$-alkyl, in particular branched $C_1$-$C_4$-alkyl, such as isopropyl. The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl, in particular methyl, ethyl, n-propyl, iso-propyl, n-butyl, isobutyl, sec-butyl, tert-butyl. Very preferred is iso-propyl.

Alkyl preferably has up to 20 carbon atom and is more preferably $C_1$-$C_7$-alkyl. Alkyl is straight-chained or branched (one or, if desired and possible, more times). Very preferred is methyl.

Halo or halogen is preferably fluoro, chloro, bromo or iodo, most preferably fluoro, chloro or bromo; where halo is mentioned, this can mean that one or more (e.g. up to three) halogen atoms are present, e.g. in halo-$C_1$-$C_7$-alkyl, such as trifluoromethyl, 2,2-difluoroethyl or 2,2,2-trifluoroethyl.

Halogenalkyl may be linear or branched and preferably comprise 1 to 4 C atoms, especially 1 or 2 C atoms. Examples are fluoromethyl, difluoromethyl, trifluoromethyl, chloromethyl, dichloromethyl, trichloromethyl, 2-chloroethyl and 2,2,2-trifluoroethyl.

Branched alkyl preferably comprises 3 to 6 C atoms. Examples are i-propyl, i- and t-butyl, and branched isomers of pentyl and hexyl. Branched $C_1$-$C_4$-alkyl is preferred, such as isopropyl.

Cycloalkyl preferably comprises 3 to 8 ring-carbon atoms, 3 or 5 being especially preferred. Some examples are cyclopropyl, cyclobutyl, cyclopentyl, cyclohexyl and cyclooctyl. The cycloalkyl may optionally be substituted by one or more substituents, such as alkyl, halo, oxo, hydroxy, alkoxy, amino, alkylamino, dialkylamino, thiol, alkylthio, nitro and cyano.

Alkenyl may be linear or branched alkyl containing a double bond and comprising preferably 2 to 12 C atoms, 2 to 8 C atoms being especially preferred. Particularly preferred is a linear $C_{2-4}$alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from $C_{1-7}$alkyl and is especially $C_2$-$C_7$-alkylene or $C_2$-$C_7$-alkylene which is interrupted by, one or more, O, NR14 or S, wherein R14 is alkyl, each of which can be unsubstituted or substituted, by one or more substituents independently selected from for example, $C_1$-$C_7$-alkyl, $C_1$-$C_7$-alkoxy-$C_1$-$C_7$-alkyl or $C_1$-$C_7$-alkoxy.

Alkenylene is a bivalent radical derived from $C_{2-7}$alkenyl and can be interrupted by, one or more, O, NR14 or S, wherein R14 is alkyl, and is unsubstituted or substituted by one or more, e.g. up to three, substitutents preferably independently selected from the substitutents mentioned above for alkylene.

Alkylamino and dialkylamino may be linear or branched. Some examples are methylamino, dimethylamino, ethylamino, and diethylamino.

Sulfonyl is (unsubstituted or substituted) $C_1$-$C_7$-alkylsulfonyl, such as methylsulfonyl, (unsubstituted or substituted) phenyl- or naphthyl-$C_1$-$C_7$-alkylsulfonyl, such as phenylmethanesulfonyl, or (unsubstituted or substituted) phenyl- or naphthyl-sulfonyl; wherein if more than one substituent is present, e.g. one to three substitutents, the substituents are selected independently from cyano, halo, halo-$C_1$-$C_7$alkyl, halo-$C_1$-$C_7$-alkyloxy- and $C_1$-$C_7$-alkyloxy. Especially preferred is $C_1$-$C_7$-alkylsulfonyl, such as methylsulfonyl, and (phenyl- or naphthyl)-$C_1$-$C_7$-alkylsulfonyl, such as phenylmethanesulfonyl. Sulfenyl is (unsubstituted or substituted) $C_{6-10}$aryl-$C_1$-$C_7$-alkylsulfenyl or (unsubstituted or substituted) $C_{6-10}$arylsulfenyl, wherein if more than one substituent is present, e.g. one to four substitutents, the substituents are selected independently from nitro, halo, halo-$C_1$-$C_7$alkyl and $C_1$-$C_7$-alkyloxy.

Alkoxy-alkyloxy may be linear or branched. The alkoxy group preferably comprises 1 to 4 and especially 1 or 2 C atoms, and the alkyloxy group preferably comprises 1 to 4 C atoms. Examples are methoxymethyloxy, 2-methoxyethyloxy, 3-methoxypropyloxy, 4-methoxybutyloxy, 5-methoxypentyloxy, 6-methoxyhexyloxy, ethoxymethyloxy, 2-ethoxyethyloxy, 3-ethoxypropyloxy, 4-ethoxybutyloxy, 5-ethoxypentyloxy, 6-ethoxyhexyloxy, propyloxymethyloxy, butyloxymethyloxy, 2-propyloxyethyloxy and 2-butyloxyethyloxy.

Alkoxyalkyl may be linear or branched. The alkoxy group preferably comprises 1 to 4 and especially 1 or 2 C atoms, and the alkyl group preferably comprises 1 to 4 C atoms. Examples are methoxymethyl, 2-methoxyethyl, 3-methoxypropyl, 4-methoxybutyl, 5-methoxypentyl, 6-methoxyhexyl, ethoxymethyl, 2-ethoxyethyl, 3-ethoxypropyl, 4-ethoxybutyl, 5-ethoxypentyl, 6-ethoxyhexyl, propyloxymethyl, butyloxymethyl, 2-propyloxyethyl and 2-butyloxyethyl.

Alkoxy being a radical or part of a radical is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$alkoxy is preferred. Alkoxy may be linear or branched and preferably comprise 1 to 4 C atoms. Examples are methoxy, ethoxy, n- and i-propyloxy, n-, i- and t-butyloxy, pentyloxy and hexyloxy.

Alkanoyl is, for example, $C_2$-$C_8$-alkanoyl and is, for example, acetyl [—C(=O)Me], propionyl, butyryl, isobutyryl or pivaloyl. $C_2$-$C_5$-Alkanoyl is preferred, especially acetyl.

Acetyl is —C(=O)$C_1$-$C_7$alkyl, preferably —C(=O)Me.

Protecting groups may be present (see also under "General Process Conditions") and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. Preferably, if two or more protecting groups are present in one intermediate mentioned herein, they are chosen so that, if one of the groups needs to be removed, this can be done selectively, e.g. using two or more different protecting groups that are cleavable under different conditions, e.g. one class by mild hydrolysis, the other by hydrolysis under harder conditions, one class by hydrolysis in the presence of an acid, the other by hydrolysis in the presence of a base, or one class by reductive cleavage (e.g. by catalytic hydrogenation), the other by hydrolysis, or the like.

As hydroxyl protecting group, any group that is appropriate for reversible protection of hydroxy groups is possible, e.g. those mentioned in the standard textbooks under "General Process Conditions". A hydroxyl protecting group may, just to mention a few examples, be selected from a group comprising (especially consisting of) a silyl protecting group, especially diary)-lower alkyl-silyl, such as diphenyl-tert-butylsilyl, or more preferably tri-lower alkylsilyl, such as tert-butyldimethylsilyl or trimethylsilyl; an acyl group, e.g. lower alkanoyl, such as acetyl; benzoyl; lower alkoxycarbonyl, such as tert-butoxycarbonyl (Boc), or phenyl-lower alk-oxycarbonyl, such as benzyloxycarbonyl; tetrahydropyranyl; unsubstituted or substituted 1-phenyl-lower alkyl, such as benzyl or p-methoxybenzyl, and methoxymethyl. Boc (selectively removable by hydrolysis) and benzyl (selectively removable by hydrogenation) are especially preferred.

Silyl is —SiRR'R", wherein R, R' and R" are independently of each other $C_{1-7}$alkyl, aryl or As amino protecting group, any group that is appropriate for reversible protection of hydroxy groups is possible, e.g. those mentioned in the standard textbooks under "General Process Conditions". An amino protecting group may, just to mention a few examples, be selected from a group comprising (especially consisting of) acyl (especially the residue of an organic carbonic acid bound via its carbonyl group or an organic sulfonic acid bound via its sulfonyl group), arylmethyl, etherified mercapto, 2-acyl-lower alk-1-enyl, silyl or N-lower alkylpyr-rolidinylidene. Preferred amino-protecting groups are lower alkoxycarbonyl, especially tert-butoxycarbonyl (Boc), phenyl-lower alkoxycarbonyl, such as benzyloxycarbonyl, fluorenyl—lower alkoxycarbonyl, such as fluorenylmethoxycarbonyl, 2-lower alkanoyl-lower alk-1-en-2-yl and lower alkoxycarbonyl-lower alk-1-en-2-yl, with most preference being given to isobutyryl, benzoyl, phenoxyacetyl, 4-tert-butylphenoxyacetyl, N,N-dimethylformamidinyl, N-methylpyrrolidin-2-ylidene or especially tert-butoxycarbonyl. Further examples of nitrogen protecting groups are acetyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tert.-butyl-dimethylsilyl, triethylsilyl (TES), triisopropylsilyl, trimethylsilyethoxymethyl (SEM), t-butoxycarbonyl (BOC), t-butyl, 1-methyl-1,1-dimethylbenzyl, (phenyl)methylbenzene, pyrridinyl and pivaloyl. Most preferred nitrogen protecting groups are acetyl, benzyl, benzyloxycarbonyl (Cbz), triethylsilyl (TES), trimethylsilyethoxymethyl (SEM), t-butoxycarbonyl (BOC), pyrrolidinylmethyl and pivaloyl. Further nitrogen protecting groups are pivaloyl, pyrrolidinylmethyl, t-butoxycarbonyl, benzyl and silyl groups, particularly silyl groups according to the formula SiR7R8R9, wherein R7, R8 and R9 are, independently of each other, alkyl or aryl. Preferred examples for R7, R8 and R9 are methyl, ethyl, isopropyl, t-butyl and phenyl.

The term "carbamate" is to be understood as an ester group —CO$_2$R attached on N, wherein R is, for example, alkyl, aryl or arylalkyl, as defined herein.

Unsubstituted or substituted aryl, being a radical or part of a radical, is preferably a mono- or polycyclic, especially monocyclic, bicyclic or tricyclic aryl moiety with 6 to 22 carbon atoms, especially phenyl (very preferred), naphthyl (very preferred), indenyl, fluorenyl, acenapthylenyl, phenylenyl or phenanthryl, and is unsubstituted or substituted by one or more, especially one to three, moieties, preferably independently selected from the group consisting of $C_1$-$C_7$-alkyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$alkanoyl)-amino, carboxy, $C_1$-$C_7$-alkoxycarbonyl, phenoxycarbonyl, naphthyloxycarbonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$alkyl)-aminocarbonyl, cyano, sulfo, sulfamoyl, N-mono- or N,N-di-($C_1$-$C_7$-alkyl, phenyl, naphthyl, phenyl-$C_1$-$C_7$alkyl and/or naphthyl-$C_1$-$C_7$alkyl)-aminosulfonyl and nitro.

Aryloxy refers to a Aryl-O— wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms independently selected from nitrogen, oxygen, sulfur, S(=O)— or S—(=O)$_2$, and is unsubstituted or substituted by one or more, e.g. up to three, substitutents preferably independently selected from the Preferred substituents are selected from the group consisting of halo, $C_1$-$C_7$-alkyl, halo-$C_1$-$C_7$-alkyl, $C_1$-$C_7$-alkoxy, halo-$C_1$-$C_7$-alkoxy, such as trifluoromethoxy and $C_1$-$C_7$-alkoxy-$C_1$-$C_7$-alkoxy. When the heterocyclyl is an aromatic ring system, it is also referred to as heteroaryl.

When referring to compounds described in the present invention, it is understood that reference is also being made to salts thereof. Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms.

The compounds of the present invention can possess one or more asymmetric centers. The preferred absolute configurations are as indicated herein specifically. However, any possible pure enantiomer, pure diastereoisomer, or mixtures thereof, e.g., mixtures of enantiomers, such as racemates, are encompassed by the present invention.

In the formulae of the present application the term „∕„ on a C-sp$^3$ indicates the absolute stereochemistry, either (R) or (S).

In the formulae of the present application the term „╱„ on a C-sp$^3$ indicates the absolute stereochemistry, either (R) or (S).

Salts are especially the pharmaceutically acceptable salts of compounds of formula XI or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds of formula XI or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalenedisulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethyl-amine or tri(2-hydroxyethyl)amine, or heterocyclic bases, for example N-ethyl-piperidine or N,N'-dimethylpiperazine.

When a basic group and an acid group are present in the same molecule, a compound of formula XI or any of the intermediates mentioned herein may also form internal salts.

For isolation or purification purposes of compounds of the formula XI or in general for any of the intermediates mentioned herein it is also possible to use pharmaceutically unacceptable salts, for example picrates or perchlorates. For therapeutic use, only pharmaceutically acceptable salts or free compounds of the formula XI are employed (where applicable comprised in pharmaceutical preparations), and these are therefore preferred at least in the case of compounds of formula I, the direct precursors of compounds of the formula XI.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter, especially to the compound(s) of the formula XI, is to be understood as referring also to one or more salts thereof or a mixture of a corresponding free compound, intermediate or starting material and one or more salts thereof, each of which is intended to include also any solvate, metabolic precursor such as ester or amide of the compound of formula XI, or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

Starting materials are especially the compounds of the formula II, III, XII and/or XIII mentioned herein, intermediates are especially compounds of the formulae I, IV, V, VI, VII, VIII, IX, X, XIV, XVI, XVII and or XVIII, in particular I, IV, V, VI, VII, VIII, IX, X and/or XIV including the preferred definitions of these.

The invention relates also to methods of synthesis of the intermediates of the formula formulae I, IV, V, VI, VII, VIII, IX, X, XIV, XVI, XVII and or XVIII, in particular I, IV, V, VI, VII, VIII, IX, X and/or XIV mentioned above from their respective precursors as mentioned above, including methods with the single steps of a sequence leading to a compound of the formulae I or XVIII, more than one or all steps of said synthesis and/or pharmaceutically active substances, especially renin inhibitors, most preferably aliskiren, including methods with the single steps of a sequence leading to a compound of the formula XI, more than one or all steps of said synthesis and/or pharmaceutically active substances, and/or their use in the synthesis of pharmaceutically active compounds, such as renin inhibitors, especially aliskiren.

General Process Conditions

The following, in accordance with the knowledge of a person skilled in the art about possible limitations in the case of single reactions, applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification. Within the scope of this disclosure only a readily removable group that is not a constituent of the particular desired end product is designated a "protecting group", unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, in "Protecting Groups", Philip J. Kocienski, 3rd Edition, GeorgThieme Verlag, Stuttgart, ISBN 3-13-137003-3 and in Jochen Lehmann, "Chemie der Kohlenhydrate: Mo-nosaccharide and Derivate" (*Chemistry of Carbohydrates: Monosaccharides and Derivatives*), Georg Thieme Verlag, Stuttgart 1974, in particular in the relevant chapters thereof. A characteristic of protecting groups is that they can be removed readily (i.e. without the occurrence of undesired secondary reactions) for example by solvolysis, reduction, photolysis or alternatively under physiological conditions (e.g. by enzymatic cleavage). Different protecting groups can be selected so that they can be removed selectively at different steps while other protecting groups remain intact. The corresponding alternatives can be selected readily by the person skilled in the art from those given in the standard reference works mentioned above or the description or the Examples given herein.

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning. Where required or desired, water-free or absolute solvents can be used.

Where required, the working-up of reaction mixtures, especially in order to isolate desired compounds or intermediates, follows customary procedures and steps, e.g. selected from the group comprising but not limited to extraction, neutralization, crystallization, chromatography, evaporation, drying, filtration, centrifugation and the like.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula I which are described as being preferred. Special preference is given to reaction conditions that are identical or analogous to those mentioned in the Examples. The invention relates also to novel starting compounds and intermediates described herein, especially those leading to compounds mentioned as preferred herein.

The invention especially relates to any of the methods described hereinbefore and hereinafter that leads to aliskiren, or a pharmaceutically acceptable salt thereof.

The following Examples serve to illustrate the invention without limiting the scope thereof, while they on the other hand represent preferred embodiments of the reaction steps, intermediates and/or the process of manufacture of aliskiren, or salts thereof.

| Abbreviations: | |
|---|---|
| δ | chemical shift |
| μl | microliter |
| Ac | acetyl |
| Bn | benzyl |
| Boc | tert-butoxycarbonyl |
| $BOC_2O$ | di-tert-butyl carbonate |
| Cbz | benzyl carbamate |
| Cbz-Cl | benzyl chloroformate |
| DCM | dichloromethane |
| de | diastereomeric excess |
| DIBAH | diisobutylaluminium hydride |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| DMSO | dimethylsulfoxide |
| ee | enantiomeric excess |
| ES | electrospray |
| ESI | electrospray ionisation |
| Et | ethyl |
| EtOAc | ethyl acetate |
| FTIR | fourier transform infrared spectroscopy |
| h | hour(s) |
| HNMR | proton nuclear magnetic resonance |
| HOBt | 1-hydroxybenzotriazole |
| HPLC | high performance liquid chromatography |
| i-Pr | isopropyl |
| iPrOAc | isopropyl acetate |
| IR | infrared |
| KHMDS | potassium bis(trimethylsilyl)amide |
| L | liter |
| LCMS | liquid chromatography-mass spectrometry |
| LDA | lithium diisopropylamide |
| LHMDS | lithium bis(trimethylsilyl)amide |
| LRMS | low resolution mass spectroscopy |
| M | molarity |
| m/e | mass-to-charge ratio |
| Me | methyl |
| mg | milligram |
| min | minute(s) |
| mL | milliliter |
| mmol(s) | millimole(s) |
| mol(s) | mole(s) |
| MS | mass spectrometry |
| NaHMDS | sodium bis(trimethylsilyl)amide |
| nm | nanometer |
| NMR | nuclear magnetic resonance |
| Pd/C | palladium on carbon |
| Ph | phenyl |
| Piv | pivaloyl |
| Piv-Cl | pivaloyl chloride |
| ppm | parts per million |
| psi | pounds per square inch |
| RT | room temperature |
| SEM | 2-(Trimethylsilyl)ethoxymethyl |
| SEM-Cl | (2-chloromethoxyethyl)-trimethylsilane |
| TBDMS | tertbutyldimethylsilyl |
| TBME | tertbutylmethylether |

-continued

Abbreviations:

| | |
|---|---|
| TEMPO | 2,2,6,6-tetramethyl-1-piperidinyloxy |
| TES | triethylsilyl |
| TFA | trifluoroacetic acid |
| THF | tetrahydrofuran |
| TLC | thin layer chromatography |
| TMEDA | N,N,N,N-tetramethylethylenediamine |
| TMS | trimethylsilyl |
| TPAP | tetrapropylammonium perruthenate |
| $t_R$ | retention time |
| Ts | tosylate/tosyl |

EXAMPLES

Example 1A

Organocatalytic Michael Addition of "In Situ" Generated Nitroethylen to Isovaleraldehyde and Reduction of the Resulting Aldehyde by NaBH$_4$ and Organocatalyst A1:
(S)-Diphenyl-prolinol-O-TMS-ether

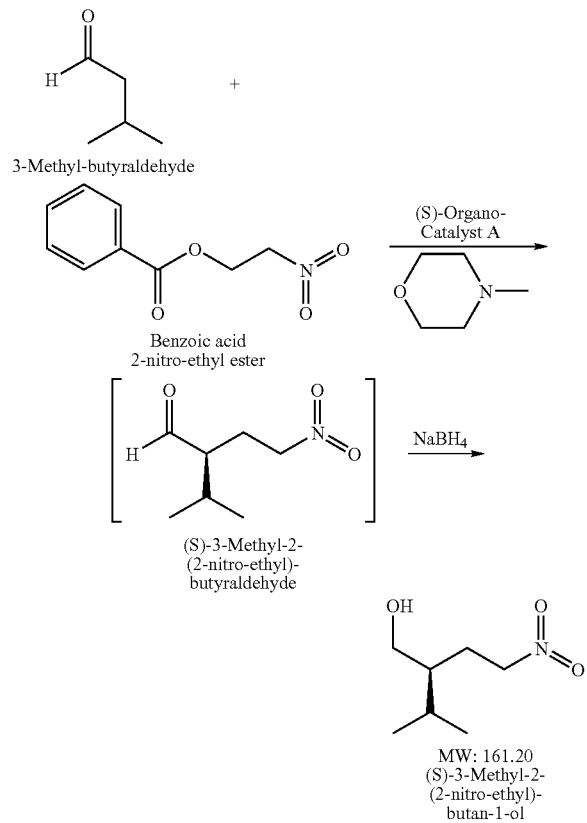

2-Nitroethyl benzoate (7.8 g, 40 mmol) and (5.3 g, 61.5 mmol) isovaleraldehyde are dissolved in a mixture of 50 ml of toluene and 5 ml of acetonitrile at room temperature. (S)-diphenylprolinol-O-TMS-ether (1.3 g, 4 mmol) is added at room temperature. To this solution is then added under stirring at 0° C. within 5 minutes (5.05 g, 50 mmol) of N-methyl morpholine to give a slightly yellow turbid solution. After 24 hours at ca. 0° C. all 2-nitroethyl benzoate is consumed (HPLC control). For work up and reduction the formed 4-nitro 2-isopropyl butyraldehyde (solution in toluene) is added slowly within 20 minutes to a well stirred solution of 4.0 g (160 mmol) of sodium borohydride in a mixture of 30 ml of water and 30 ml of ethanol. Vigorous hydrogen evolution is observed at the beginning. After 30 minutes the reduction is complete. The reaction mixture is quenched with aqueous citric acid solution. The toluene phase is separated and the aqueous phase is extracted with 2 portions (50 ml) of toluene. The combined organic phases are washed with 1N HCl, sat. bicarbonate and finally with H$_2$O (each 2×50 ml). The toluene phase is dried over MgSO$_4$ and evaporated in vacuum to a yellow oil.

Determination of the enantiomeric ratio by HPLC at 205 nm with a Chiralpak AD-H column showed 85% enantiomer A and 15% enantiomer B.

According to lit. ref. the enantiomer A has the shown configuration (S).

The crude product was purified by column chromatography on silica gel (200 g) with heptane: ethyl acetate (2:1) to give in the pure fractions 3-methyl-2-(2-nitroethyl)-2-butan-1-ol as a slightly yellow oil.

$^1$H-NMR: (600 MHz, CDCl$_3$); $\delta_H$ (ppm) 4.59-4.50 (2H, m, CH$_2$NO$_2$), 3.76-3.72 (1H, m, CH$_2$OH), 3.63-3.58 (1H, m, —CH$_2$OH), 2.20-2.14 (1H, m, CH$_2$), 2.07-2.01 (1H, m, CH$_2$), 1.82-1.74 (1H, m, —CH(CH$_3$)$_2$), 1.48-1.43 (1H, m, CH), 1.29 (1H, t, J 4.6 Hz, —OH), 0.94 (6H, dd, J 7 Hz, —CH$_3$).

$^{13}$C-NMR: (150 MHz, CDCl$_3$); $\delta_C$ (ppm) 74.84 (CH$_2$NO$_2$), 63.95 (CH$_2$OH), 43.69 (CH), 28.70 (CH(CH$_3$)$_2$), 27.21 (CH$_2$), 19.68 (CH$_3$), 19.35 (CH$_3$).

MS: (ES−); [M−H]$^-$=160

IR: (FTIR-Microscopy in transmission) 3384 (br, OH), 2962, 2877 (CH), 1551 (asNO$_2$), 1466, 1435 (CH), 1385 (syNO$_2$) [cm$^{-1}$]

$^1$H-NMR: of the corresponding intermediate nitro aldehyde: (400 MHz, CDCl$_3$); $\delta_H$ (ppm) 4.57-4.48 (1H, m, CHNO$_2$), 4.40-4.30 (1H, m, CHNO$_2$), 2.42-2.35 (1H, m), 2.35-2.15 (2H, brm), 2.15-2.05 (1H, m), 1.07 (3H, d, CH$_3$), 0.99 (3H, d, CH$_3$)

Example 1B

Organocatalytic Michael Addition of "In Situ" Generated Nitroethylen to Isovaleraldehyde and Reduction of the Resulting Aldehyde by NaBH$_4$ with Organocatalyst A2,
(S)-Diphenyl-prolinol-O-TBDMS-ether and Different Work Up 2-Nitroethyl benzoate (11.71 g, 60 mmol) and (9.3 g, 108 mmol, 1.8 equ. val) isovaler-aldehyde are dissolved in a mixture of 75 ml of toluene and 7.5 ml of acetonitrile at room temperature. (S)-diphenylprolinol-O-TBDMS-ether (1.76 g, 4.8 mmol, 8 mol %) is added at room temperature. The reaction mixture is cooled to 0° C. and 6.98 g (69 mmol) of N-methyl-morpholine is added via dropping funnel in 30 minutes. The reaction mixture is stirred over night at 0° C. and conversion is controlled by HPLC to show 90% conversion. Additional N-methylmorpholine is added and stirring is continued at room temperature for 5 hours. To the reaction mixture is added 30 ml of water for extraction of salts, then further extracted with aqu. Citric acid solution (30 ml) and finally with water (30 ml). This toluene phase is then added slowly at 0° C. to a solution of 3.4 g of sodium borohydride in 20 ml of water and 20 ml of ethanol under stirring. After 1 hour the reaction is complete and after work up with 1 N HCl (3×70 ml), 10% bicarbonate solution (2×70 ml) and finally with brine (70 ml) crude product is obtained, which is almost pure according to NMR. The enantiomeric ratio measured as described above was 96.4% enantiomer A and 3.6% enantiomer B. To get a second crop of yield the acidic aqu. phases were combined and extracted with dichloromethane (2×30 ml) to give additional crude product which was combined with the first part. Analytical data as in Example 1A.

Example 2

Organocatalytic Michael Addition of "In Situ" Generated Nitroethylen to Propionaldehyde and Reduction of the Resulting Aldehyde by NaBH$_4$

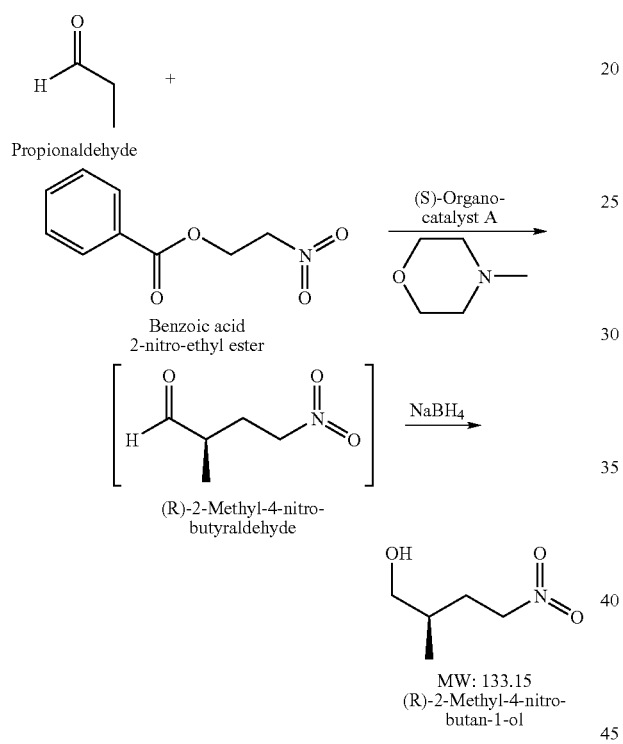

The organocatalytic reaction was performed as in Example 1:

2-Nitroethyl benzoate (4.68 g, 24 mmol) and (3.5 g, 60 mmol) propionaldehyde are dissolved in 30 ml of hexane. (S)-diphenylprolinol-O-TMS-ether (1.95 g, 6 mmol) is added at room temperature. To this solution is then added under stirring at 0° C. within 3 hours (3.45 g, 30 mmol) of N-ethyl morpholine as hexane solution to give a slightly yellow turbid solution. After 3 hours stirring at ca. 0° C. all 2-nitroethyl benzoate is consumed (HPLC control). To the reaction mixture is then added 15 ml of ethanol followed by portionwise addition of 1 g (40 mmol) of sodium borohydride. The reaction mixture becomes very thick and therefore 20 ml of water is added to get a clear solution. Hydrogen evolution is observed at the beginning. After 30 minutes the reduction is complete. The reaction mixture is quenched with aqueous 2N HCl and the pH was adjusted to 3. The reaction mixture is concentrated in vacuum and then extracted with 60 ml ethyl acetate. The ethyl acetate phase is washed with saturated sodium bicarbonate (4×20 ml) and finally with 0.5 N aqueous HCl (2×20 ml). The ethyl acetate phase is evaporated in vacuum to give a yellow orange oil. The enantiomeric ratio of the crude material before chromatography determined by HPLC at 205 nm with a Chiralpak AD-H column was 85% enantiomer A and 15% enantiomer B.

Spectroscopic data of the (R)-2-Methyl-4-nitro-butan-1-ol $^1$H-NMR: (400 MHz, d$_6$-DMSO), $\delta_H$ (ppm) $\delta$=0.86 (3H, d, J=6.76 Hz, CH$_3$), 1.55-2.02 (3H, brm, —CH, —CH$_2$), 3.26 (2H, m, CH$_2$—OH), 4.56-4.62 (3H, m, CH$_2$NO$_2$ & OH)

$^{13}$C-NMR: (400 MHz, d$_6$-DMSO), $\delta$ (ppm) $\delta$=15.9, 30.3, 32.4, 65.2, 73.7

MS: [MH—H$_2$O]$^+$=115.9, [M–H]$^-$=132.2

IR: (FTIR-microscopy in transmission) 3368 (CH), 2880-2966 (CH), 1552 (as-NO$_2$), 1435 (CH), 1381 (sy-NO$_2$) [cm$^{-1}$]

Spectroscopic data of the corresponding aldehyde (2-Methyl-4-nitro-butyraldehyde)

$^1$H-NMR: (400 MHz, d$_6$-DMSO), $\delta_H$ (ppm) $\delta$=1.09 (3H, d, J=7.26 Hz, CH$_3$), 1.89-2.34 (2H, m), 2.52 (1H, m), 4.62 (2H, m, CH$_2$NO$_2$), 9.58 (1H, s)

$^{13}$C-NMR: (150 MHz, d$_6$-DMSO), $\delta$ (ppm) $\delta$=12.5, 26.5, 42.1, 72.8, 204.0

MS: (MH—HNO$_2$)$^+$ 84.9, (M–H—HNO2)$^+$ 83.3, (M–H)$^-$ 130.1

IR: (FTIR-microscopy in transmission) 2833-2972 (CH), 2729 (Fermi-Res. aldehyde., 1725(C=O), 1553 (as-NO$_2$), 1434 (CH) 1382 (sy-NO$_2$)

Example 3

Organocatalytic Michael Addition of "In Situ" Generated Nitroethylen to Isovaleraldehyde and Reduction of the Resulting Aldehyde by NaBH$_4$ Organocatalyst B; (S)-Pyrrolidine-tetrazole

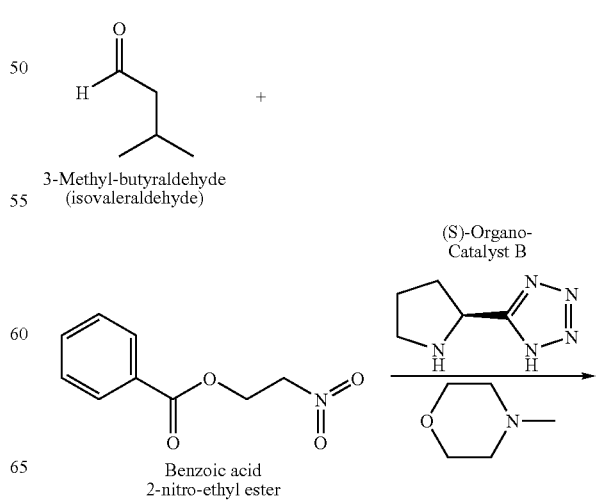

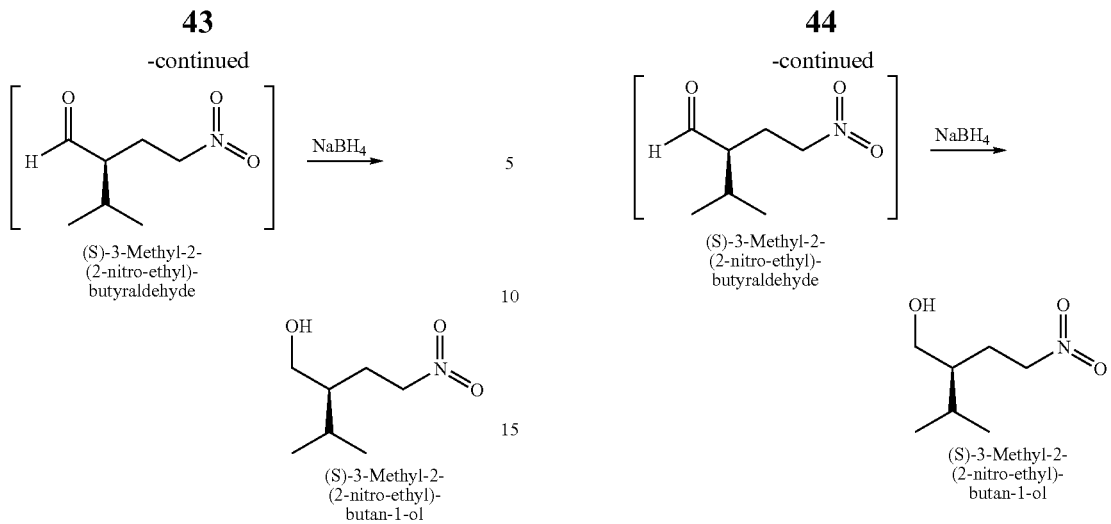

2-Nitroethyl benzoate (0.39 g, 2 mmol) and (0.26 g, 3 mmol) isovaleraldehyde are dissolved in 4 ml of acetonitrile at room temperature.

(S)-pyrrolidine-tetrazol catalyst B (42 mg, 0.3 mmol) is added at room temperature. To this solution is then added under stirring at −20° C. within 5 minutes (0.25 g, 2.5 mmol) of N-methyl morpholine to give a slightly yellow solution. After 16 hours at −20° C. all 2-nitroethyl benzoate was consumed (HPLC control). Reduction with sodium borohydride and workup was performed as in Example 2.

The enantiomeric ratio determined by HPLC at 205 nm with a Chiralpak AD-H column was 82% enantiomer A and 18% enantiomer B.

Analytical data as in Example 1A.

Example 4

Organocatalytic Michael Addition of "In Situ" Generated Nitroethylen to Isovaleraldehyde and Reduction of the Resulting Aldehyde by NaBH$_4$ Organocatalyst C, (S)-Proline

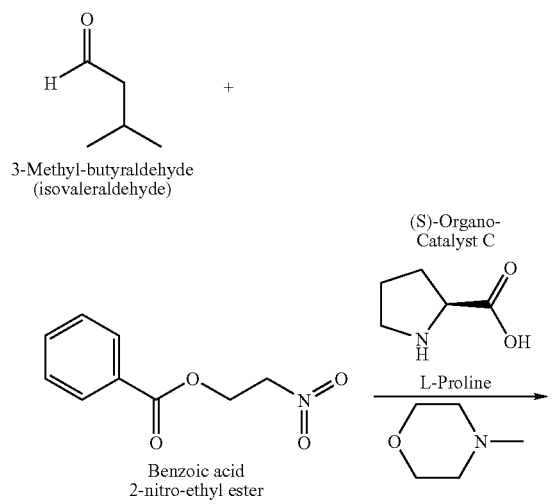

2-Nitroethyl benzoate (0.39 g, 2 mmol) and (0.26 g, 3 mmol) isovaleraldehyde are dissolved in 4 ml of acetonitrile at room temperature. L-proline (catalyst C) (69 mg, 0.6 mmol) is added at room temperature. To this solution is then added under stirring at −20° C. within 5 minutes (0.25 g, 2.5 mmol) of N-methyl morpholine to give a slightly yellow solution. After 16 hours at −20° C. all 2-nitroethyl benzoate was consumed (HPLC control). Reduction with sodium borohydride and workup is done as in Example 2. The enantiomeric ratio determined by HPLC at 205 nm with a Chiralpak AD-H column was 68% enantiomer A and 32% enantiomer B.

Analytical data as in Example 1A.

Example 5

Organocatalytic Nitro Aldol Reaction of methyl 4-nitrobutanoate and (S)-3-Benzyloxymethyl-4-methylpentanal catalysed by (−)sparteine under Solvent-Free Conditions

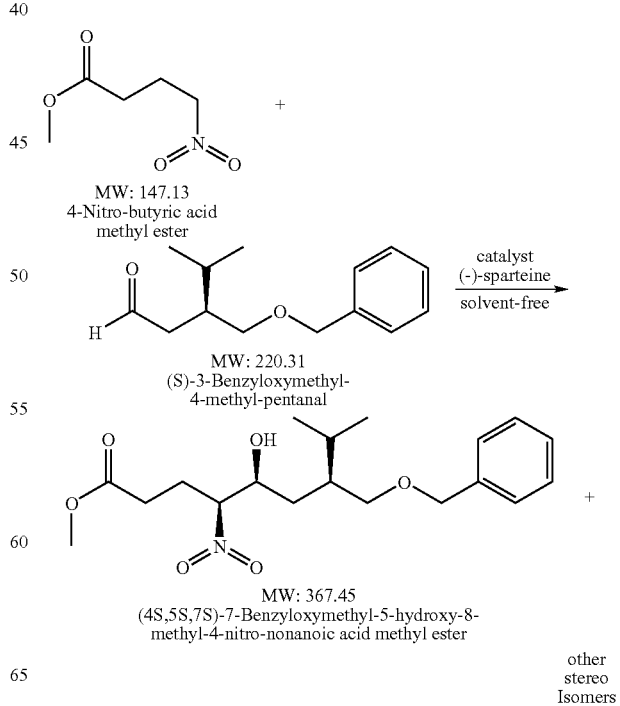

Methyl 4-nitrobutyrate (1.25 g, 7.64 mmol) and 3.01 g (S)-3-Benzyloxymethyl-4-methyl-pentanal (13.66 mmol) from example 11 and 0.53 g (−)-sparteine are mixed together and are stirred without any additional solvent at room temperature for 18 hours. After that time HPLC control showed almost complete conversion of the nitro butyrate. The reaction mixture is purified by column chromatography on silica gel (heptane/ethyl acetate=3:1). The product containing fractions were collected and combined to give the nitroaldol product (mixture of 4 stereoisomers according to HPLC, LCMS and $^1$H-NMR).

$^1$H-NMR: (400 MHz, d$_6$-DMSO; δ$_H$ (ppm), stereoisomer mixture 0.8-0.9 (6H, m-d, —CH$_3$), 1.25-1.50 (2H, brm, —CH—), 1.62-1.87 (2H, brm, —CH—), 2.0-2.45 (4H, brm), 3.35-3.45 (2H, brm, —CH$_2$O), 3.60 (3H, s, —OCH$_3$), 3.78-3.88 (m, CHOH, from 1 epimer) and 3.95-4.05 (m, CHOH, from 2. epimer), 4.40-4.46 (2H, dd, ab, —OCH$_2$Ph), 4.45-4.60 (1H, brm, CH—NO$_2$), 5.82-5.90 (1H, m, —OH), 7.22-7.36 (5H, m, Ar)

MS: [MH]$^+$=368, [M+NH$_4$]$^+$=385

IR: (FTIR-microscopy in transmission) 3404 (br, OH), 3064, 3031 (Bn-CH), 2958, 2874 (al.CH), 1738 (C=O), 1550 (asNO$_2$) 1369 (syNO$_2$), 1175, 1092, 1074 (C—O—C), 741, 700 [cm$^{-1}$]

Example 6

Hydrogenation of (4S,5S,7S)-7-Benzyloxymethyl-5-hydroxy-8-methyl-4-nitro-nonanoic acid methyl ester with Ra—Ni to Benzylprotected Pyrrolidone

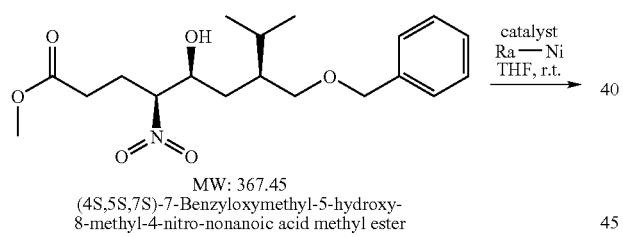

MW: 367.45
(4S,5S,7S)-7-Benzyloxymethyl-5-hydroxy-8-methyl-4-nitro-nonanoic acid methyl ester

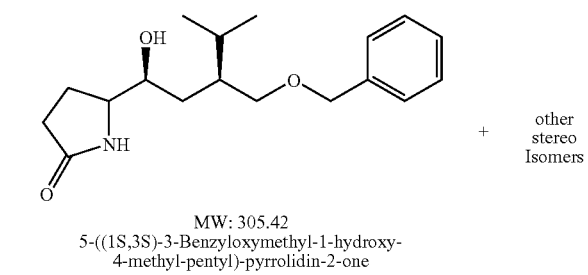

MW: 305.42
5-((1S,3S)-3-Benzyloxymethyl-1-hydroxy-4-methyl-pentyl)-pyrrolidin-2-one 1.0 g (2.72 mmol) of (4S,5S,7S)-7-Benzyloxymethyl-5-hydroxy-8-methyl-4-nitro-nonanoic acid methyl ester from example 5 are dissolved in 25 ml of dry THF and are then hydrogenated over Ra—Ni (Degussa) at normal pressure and room temperature over night (ca. 16 hours). After complete conversion the catalyst is filtered off and the solvent is evaporated to give a yellow oil. According to $^1$H-NMR, IR, MS and HPLC the obtained oil is a mixture of 4 diastereoisomeric lactam compounds.

$^1$H-NMR: (400 MHz, d$_6$-DMSO; δ$_H$ (ppm), isomeric mixture 0.81-0.88 (6H, mult. d, —CH$_3$), 1.10-1.42 (2H, brm, —CH), 1.60-1.75 (1H, brm, CH), 1.75-2.15 (5H, brm, —CH$_2$), 3.25-3.45 (4H, brm, N—CH, O—CH, —OCH$_2$), 4.38-4.48 (2H, —O—CH$_2$—Ph), 4.58-4.64 (1H, m, —OH), 7.22-7.38 (5H, m, arom.H), 7.46 & 7.54 (1H, two d, NH, for 2 diastereomers).

LC-MS: MH$^+$=306 (4 isomers)

IR: (FTIR-microscopy in transmission) 3269 (br, NH,OH), 2957, 2872 (aliph.CH), 1687 (amide, C=O), 1455, 1367 (CH$_3$), 1094, 1074 (C—O—C), 738, 699 [cm$^{-1}$]

Example 7

Hydrogenation (S)-5-(1S,3S)-3-Benzyloxymethyl-1-hydroxy-4-methyl-pentyl)-pyrrolidin-2-one to (S)-5-((1S,3S)-1-Hydroxy-3-hydroxymethyl-4-methyl-pentyl)-pyrrolidin-2-one

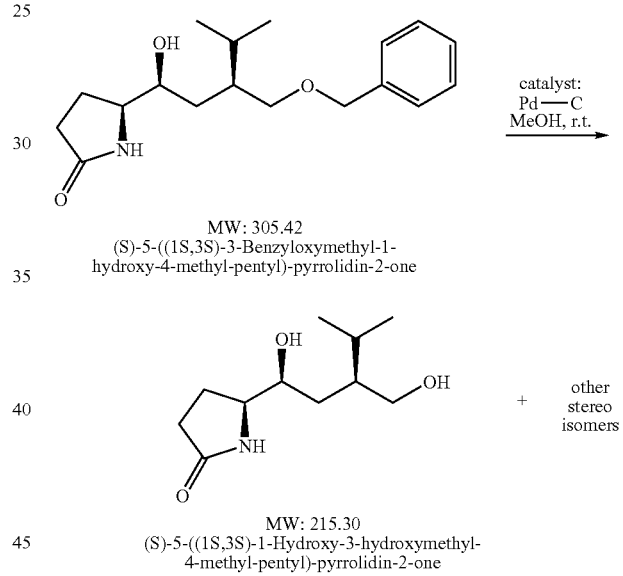

MW: 305.42
(S)-5-((1S,3S)-3-Benzyloxymethyl-1-hydroxy-4-methyl-pentyl)-pyrrolidin-2-one MW: 215.30
(S)-5-((1S,3S)-1-Hydroxy-3-hydroxymethyl-4-methyl-pentyl)-pyrrolidin-2-one 0.78 g (2.55 mmol) of (S)-5-((1S,3S)-3-Benzyloxymethyl-1-hydroxy-4-methyl-pentyl)-pyrrolidin-2-one from example 6 was hydrogenated in 20 ml methanol between room temperature and 40° C. and normal pressure over 0.4 g of Pd/C (10%) for 24 hours. After complete conversion the catalyst is filtered off and the solvent is evaporated in vacuum to give the expected debenzylated product as a colourless oil.

$^1$H-NMR: (400 MHz, d$_6$-DMSO); δ$_H$ (ppm), isomeric mixture (4 isomers) 0.75-0.9 (6H, mult. d, —CH$_3$), 1.1-1.3 (2H, brm, CH), 1.4-1.5 (1H, m, CH), 1.65-2.15 (6H, brm, —CH$_2$), ca. 3.3-3.45 (2H, brm, —CH$_2$—OH), 4.3 (1H, m, —N=C H—), 4.45-4.6 (t, —CH$_2$OH), 4.75-4.85 (2× d, —CHOH), 7.44, 7.46, 7.52, 7.53 (1H, 4 diff. singletts, NH-amide)

MS: [M+H]$^+$=216

IR: (FTIR microscopy in transmission) 3323 (br, —OH, —NH), 2957, 2875 (aliph. CH), 1684 (C=O, lactam), [cm$^{-1}$]

Example 8

Oxidation of S)-5-((1S,3S)-1-Hydroxy-3-hydroxymethyl-4-methyl-pentyl)-pyrrolidin-2-one to (S)-5-((S)-4-Isopropyl-5-oxo-tetrahydro-furan-2-yl)-pyrrolidin-2-one

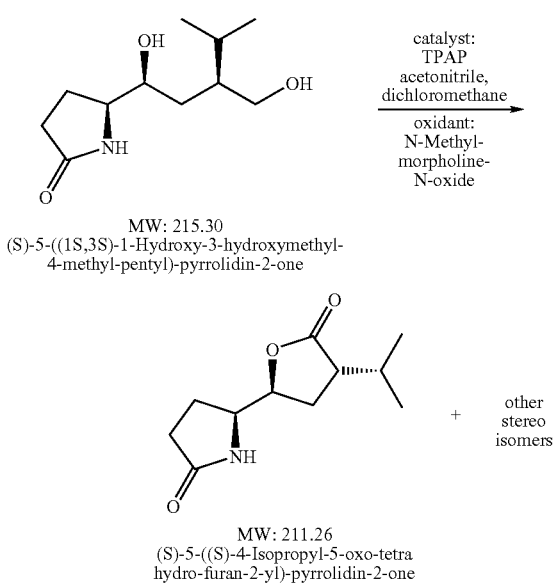

0.400 g (1.85 mmol) of the lactam-diol product of example 7 is dissolved in 18 ml of dichloromethane and 2 ml of acetonitrile. 1 g of molecular sieves (0.3 nm, perlform, Merck) and 0.75 g of 4-methylmorpholine-4-oxyde as oxidant is added at room temperature. Then 64 mg of TPAP (tetrapropyl ammonium perruthenate) as catalyst is added. The reaction mixture is first stirred at room temperature for 6 hours, then additional 64 mg of catalyst is added because only slow conversion is observed. The reaction mixture is then stirred over night at room temperature and finally at reflux for 3 hours. After complete conversion the solvents are evaporated in vacuum and the residue is dissolved again in 30 ml of dichloromethane. The dichloromethane solution is filtered over $SiO_2$ (10 g) and eluted with dichloro methane. The collected fractions are evaporated in vacuum to give 270 mg of a pink, yellow coloured oil, which was again dissolved in dichloromethane. After washing with bisulfite, 0.5 N HCl, drying over $MgSO_4$ and evaporation gives a yellow coloured oil. The oil could be crystallized from diethyl ether and hexane to give off white crystals. The crystals are a mixture of 2 major stereoisomers (ca. 1:1) according to NMR.

$^1$H-NMR: (400 MHz, $d_6$-DMSO); $\delta_H$ (ppm), mixture of isomers. 0.80-0.90 (3H, mult. d, —$CH_3$), 0.92-1.02 (3H, mult. d, —$CH_3$), 1.60-1.80 (1H, brm, —CH), 1.95-2.25 (6H, brm, —$CH_2$ & —CH), 2.60-2.80 (1H, brm, —CH), 3.60-3.78 (1H, brm, N—CH), 4.30-4.42 (1H, brm, O—CH), 7.92 & 7.96, amide-H).

MS: $[M+H]^+=212$, $[2M+H]^+=423$

IR: (FTIR microscopy in transmission) 3239 (br, NH), 2962, 2875 (aliph. CH), 1765 (s, C=O, lacton), 1685 (s, C=O, lactam), 1180 (C=O), [$cm^{-1}$]

Example 9

Organocatalytic nitro aldol reaction of (S)-3-Methyl-2-(2-nitro-ethyl)-butan-1-ol and (S)-3-Benzyloxymethyl-4-methyl-pentanal catalysed by (−)sparteine

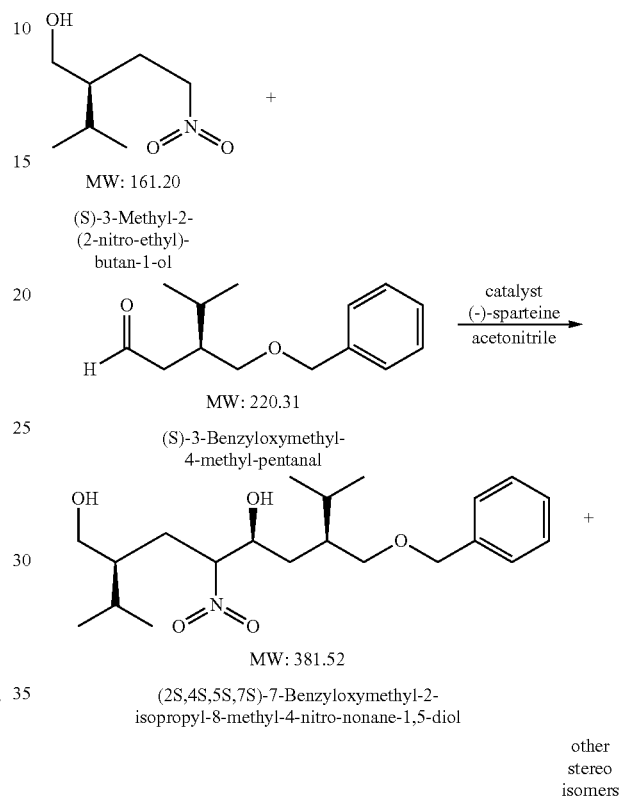

In a flask is dissolved 1.5 g (6.77 mmol) of (S)-3-Benzyloxymethyl-4-methyl-pentanal and 0.84 g (5.21 mmol) of 3-methyl-2-(nitro-ethyl)-butan-1-ol VI in 2 ml of acetonitrile. To this solution is added 360 mg of (−)-sparteine. The solution is stirred over night at room temperature. HPLC control showed still unreacted nitro compound. Therefore additional aldehyde (500 mg) is added and stirring was continued for further 24 h. The solvent is evaporated and the oily residue is chromatographed on silica gel with heptane/EtOAc (2:1). The product containing fractions are combined to give a yellow oil which consists according to LCMS mostly as mixture of 3 stereoisomers with one as the major isomer.

$^1$H-NMR: (500 MHz, $d_6$-DMSO); $\delta_H$ (ppm), isomeric mixture, complex proton NMR 0.76-0.88 (12H, mult. d, 4×—$CH_3$), 0.99 (m, CH), 1.1-1.9 (sev. brm., —CH & $CH_2$), 3.35-3.45 (4H, brm, —$CH_2$O—), 3.7-3.95 (sev. brm, —CH—OH), 4.4-4.55 (2H, ab, —$OCH_2$Ph), 4.6-4.65 (1H, brm, —CH—$NO_2$), 5.28-5.38 (1H, mult. d, —CH—OH), 7.25-7.4 (5H, m, ar. H).

MS: $[M+H]^+=382.2$; $[M+NH_4]^+=399.2$

IR: (FTIR microscopy in transmission) 3396 (br, OH), 3089, 3065, 3031 (CH, Bn-H), 2959-2875 (al. CH), 1552 (as-$NO_2$), 1466, 1455 (ar.CH), 1369 (sy-$NO_2$), 1090, 1072 (C—OH, C—O—C), 739, 699 (ar, monosub.), [$cm^{-1}$]

Example 10

Substitution of ((S)-2-Chloromethyl-3-methyl-butoxymethyl)-benzene with cyanide (starting material see: J. Maibaum et al., Helv. Ch. Acta, 86, 2848, 2003)

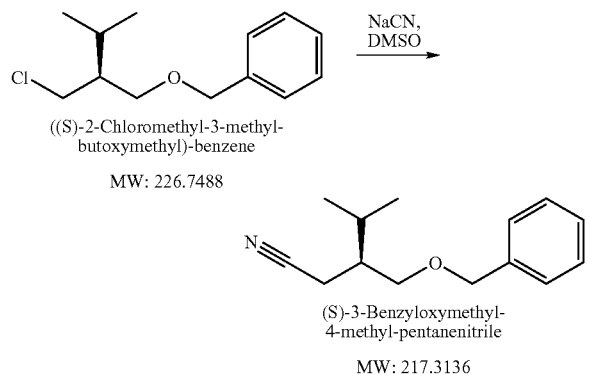

((S)-2-Chloromethyl-3-methyl-butoxymethyl)-benzene
MW: 226.7488

(S)-3-Benzyloxymethyl-4-methyl-pentanenitrile
MW: 217.3136

A flask is charged with 25.93 g (0.53 mol) of dry sodium cyanide and 195 ml of dry DMSO. The mixture is warmed up to an internal temperature of 90° C. To this mixture is added via a dropping funnel a solution of 100 g (0.441 mol) of ((S)-2-Chloromethyl-3-methyl-butoxymethyl)-benzene dissolved in 55 ml of dry DMSO under stirring during 1 hour. After additional 3 h at 90° C. the reaction mixture (slightly yellow suspension) is cooled to room temperature and 500 ml of water and 500 ml of toluene is added. The aqueous phase is separated and back extracted with additional 200 ml of toluene. The combined organic phases are washed twice with brine (200 ml) and are dried over $Na_2SO_4$, then filtered and evaporated in vacuum and finally in high vacuum to give almost pure nitrile as an oil.

$^1$H-NMR: (400 MHz, $d_6$-DMSO); $\delta_H$ (ppm)
0.88-0.89 (3H, d, $CH_3$), 0.90-0.91 (3H, d, $CH_3$), 1.70-1.83 (2H, m, 2×CH), 2.48-2.64 (2H, ddd, abx, $CH_2CN$), 3.38-3.42 (1H, dd, $OCH_2$), 3.51-3.55 (1H, dd, $OCH_2$) 4.45-4.53 (2H, dd, ab, $PhCH_2O$), 7.32-7.39 (5H, m, arom.H).

MS: [M+H]$^+$=218, [M+NH$_4$]$^+$=235

IR: (FTIR-Microscopy in transmission) 3089, 3064 (ar.CH), 2964, 2875 (al. CH), 2244 (CN), 1455 (Ph), 1369 ($CH_3$), 1103 (C—O—C) 739, 699 (arCH) [cm$^{-1}$]

Example 11

Reduction of (S)-3-Benzyloxymethyl-4-methyl-pentanenitrile with DIBAH to aldehyde

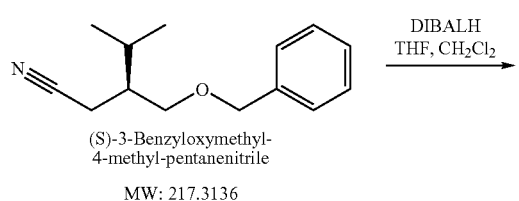

(S)-3-Benzyloxymethyl-4-methyl-pentanenitrile
MW: 217.3136

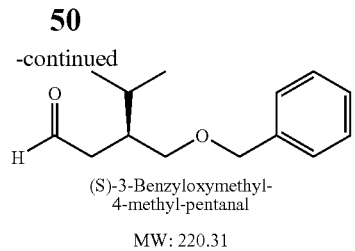

(S)-3-Benzyloxymethyl-4-methyl-pentanal
MW: 220.31

A flask is charged with 12.0 g (0.0552 mol) of "(S)-3-benzyloxymethyl-4-methyl-pentane-nitrile and dissolved in 50 ml of THF. The solution is cooled to 0-5° C. and 100 ml of a fresh dichloromethane solution of DIBAH (0.080 mol, 1.45 equival.) is added via a dropping funnel during 1 hour. After stirring for an additional hour HPLC shows complete conversion. The reaction mixture is quenched on 1 N HCl (200 ml) at 0° C. under stirring. Additional 200 ml THF is added and the phases are separated. The aqueous phase is 3-times extracted with 60 ml TBME. The combined organic phases are dried over $MgSO_4$. After filtration the solvents are evaporated under reduced pressure and finally in high vacuum to give the product as an oil.

$^1$H-NMR: (400 MHz, $d_6$-DMSO); $\delta_H$ (ppm) $\delta$=0.81-0.82 (3H, d, —$CH_3$), 0.85-0.86 (3H, d, —$CH_3$), 1.68-1.80 (1H, m, CH), 2.08-2.19 (1H, m, CH), 2.25-2.30 (1H, ddd, —$CH_2$), 2.37-2.42 (1H, ddd, $CH_2$), 3.28-3.32 (1H, dd, —$OCH_2$), 3.43-3.46 (1H, dd, —$OCH_2$), 4.40-4.44 (2H, dd, $PhCH_2O$), 7.22-7.38 (5H, m, arom.H), 9.65 (1H, t, ald.H)

MS: [M–H]$^-$=219.3

IR: (FTIR-Microscopy in transmission) 3088, 3031 (arCH), 2960, 2873 (al.CH), 2723 (Fermi Res. Ald.), 1724 (C=O), 1465, 1368 ($CH_3$), 1103 (C—O—C), 737, 698 (monoCH), [cm$^{-1}$]

$[\alpha]_D$=–12.6° (0.983% in MeOH)

Example 12

Hydrogenation of (2S,4S,5S,7S)-7-Benzyloxymethyl-2-iso-propyl-8-methyl-4-nitro-nonane-1,5-diol with Raney-Ni in the presence of $Boc_2O$

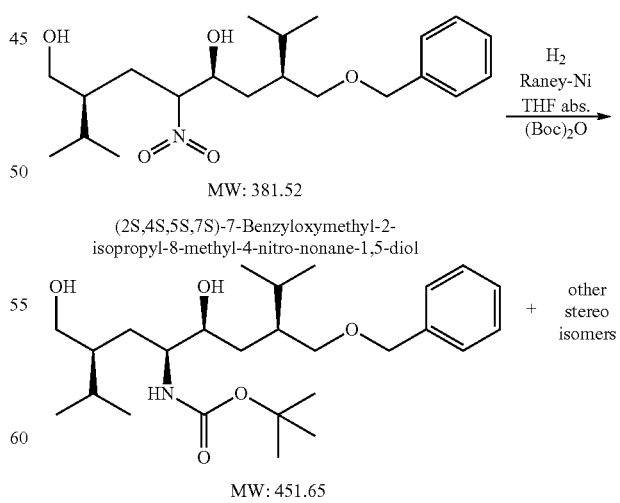

(2S,4S,5S,7S)-7-Benzyloxymethyl-2-isopropyl-8-methyl-4-nitro-nonane-1,5-diol
MW: 381.52

+ other stereo isomers

[(1S,2S,4S)-4-Benzyloxymethyl-2-hydroxy-1-((S)-2-hydroxymethyl-3-methyl-butyl)-5-methyl-hexyl]-carbamic acid tert-butyl ester
MW: 451.65

0.64 g (1.67 mmol) of the nitroaldol product from example 9 and 0.42 g (1.92 mmol) of Boc$_2$O are dissolved in 20 ml of ethanol. Then 0.2 g of Raney-Ni (B113 W Degussa) is added.

The mixture is hydrogenated at normal pressure and room temperature over night. Additional Ra—Ni (0.4 g) is added in two portions with a time interval of 6 hours and hydrogenation is continued until >95% of the calculated hydrogen is consumed and HPLC showed complete conversion. The catalyst is filtered off and washed with 2×10 ml of ethanol. The solvent is removed in vacuum to give an yellow oil which was purified by chromatography to remove excess Boc$_2$O giving a mixture of stereoisomers with complex proton NMR spectrum.

MS: [M+H]$^+$=452.3, 352.3 (MH$^+$-Boc)

Example 13

Hydrogenation of [(1S,2S,4S)-4-Benzyloxymethyl-2-hydroxy-1(S)-2-hydroxymethyl-3-methyl-butyl)-5-methyl-hexyl]-carbamic acid tert-butyl ester to triol

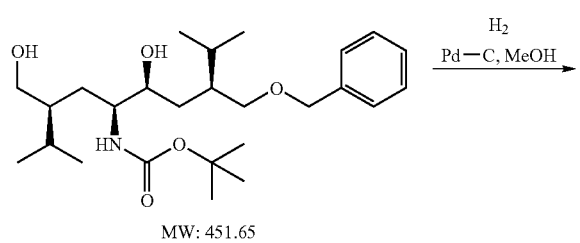

MW: 451.65

[(1S,2S,4S)-4-Benzyloxymethyl-2-hydroxy-1-((S)-2-hydroxymethyl-3-methyl-butyl)-5-methyl-hexyl]-carbamic acid tert-butyl ester

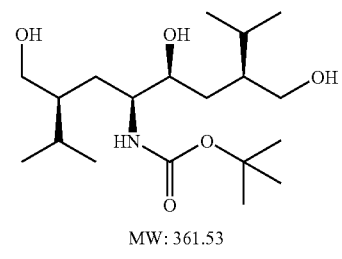

MW: 361.53

[(1S,2S,4S)-2-Hydroxy-4-hydroxymethyl-1-((S)-2-hydroxymethyl-3-methyl-butyl)-5-methyl-hexyl]-carbamic acid tert-butyl ester 0.45 g (1 mmol) of N-BOC-benzyloxy protected compound (IXa) from example 12 is hydrogenated in 20 ml methanol at room temperature and normal pressure with 0.2 g of Pd/C (10%) for 24 hours. After complete conversion the catalyst is filtered off, catalyst residue is washed with methanol and the solvent is evaporated in vacuum to give (0.35 g) of the expected debenzylated crude product as a colourless oil as a mixture of stereoisomers.

MS: [M+H]+=362.5

Example 14A

Oxidation of [(1S,2S,4S)-2-Hydroxy-4-hydroxymethyl-1-(S)-2-hydroxy-methyl-3-methyl-butyl)-5-methyl-hexyl]-carbamic acid tert-butyl ester with catalytic tetrapropylammonium perruthenate (TPAP) and N-Methyl-morpholine N-oxide

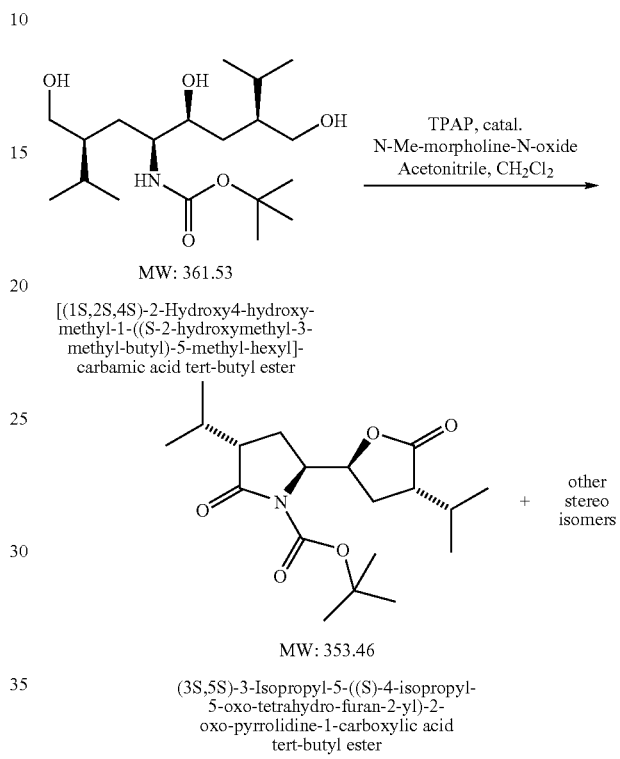

1.08 g (3.0 mmol) of the NH-BOC-triol compound of example 13 is dissolved in 15 ml of dichloromethane and 5 ml of acetonitrile. 1 g of molecular sieves (0.3 nm, perlform, Merck) and 3.65 g of 4-methylmorpholine-4-oxyde-hydrate (27 mmol) as oxidant are added at room temperature. Then 176 mg (0.5 mmol) of TPAP (tetrapropyl ammonium perruthenate) as catalyst is added. The reaction mixture is first stirred at room temperature for 3 hours, then is warmed up to reflux over night. After complete conversion (HPLC, 205 nm) the solvents are evaporated in vacuum and the residue is dissolved again in 30 ml of dichloro-methane. The dichloromethane solution is filtered over SiO$_2$ (15 g) to remove TPAP and eluted with dichloromethane. The product containing fractions are evaporated in vacuum to give 870 mg of a pink, yellow coloured oil, which is again dissolved in dichloromethane. After washing with bisulfite, 0.5 N HCl, drying over MgSO$_4$ and evaporation, a pink-yellow coloured oil is obtained.

The oil is crystallized from diethyl ether and hexane to give off white crystals. The crystals are a mixture of stereoisomers. The $^1$H-NMR-signals of the (S,S,S,S)-stereoisomer is identified in the mixture.

$^1$H-NMR (400 MHz, CDCl$_3$): 4.52-4.48 (m, 1H, 4.34-4.29 (m, 1H), 2.68-2.62 (m, 1H), 2.55-2.49 (m, 1H), 2.24-2.08 (m, 4H), 2.03-1.94 (m, 1H), 1.81-1.75 (m, 1H), 1.52 (s, 9H), 1.02-0.98 (pst, 6H), 0.92-0.91 (d, 3H, 0.85-0.84 (d, 3H)

MS: MH$^+$=354

IR: 1777-1760 (Lactone/Lactam/-Boc), 1185 Boc cm$^{-1}$ (FTIR-Microscopy in transmission)

Example 14B

Oxidation of [(1S,2S,4S)-2-Hydroxy-4-hydroxymethyl-1-((S)-2-hydroxy-methyl-3-methyl-butyl)-5-methyl-hexyl]-carbamic acid tert-butyl ester with catalytic Tempo and bleach (NaOCl) as oxidant

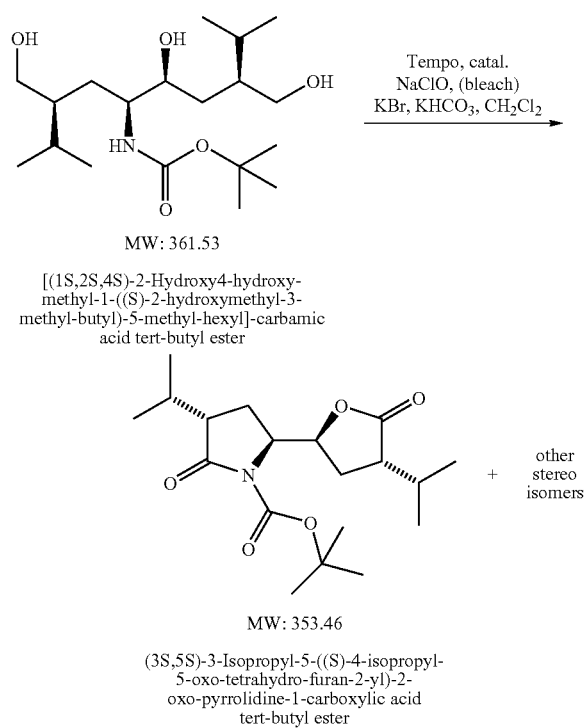

1.0 g (2.76 mmol) of "N-Boc-triol" compound from example 13 is dissolved in 10 ml of dichloromethane. The solution is cooled to 0° C. and 18 mg of Tempo as catalyst is added. 5 ml of an aqueous solution (25%) of potassium bromide and 12 ml of an aqueous solution (14%) of KHCO$_3$ are added under stirring. To this biphasic mixture is added, via a dropping funnel, an aqueous solution (40 ml), (8.5%) of NaOCl (bleach) under rapid stirring over 20 minutes. The colour of the reaction mixture changes to orange, then after 15 min to yellow. Upon 30 minutes of stirring, another 18 mg of Tempo, 5 ml of KBr solution and 10 ml KHCO$_3$ solution are added. Then again 5 ml of an aqueous solution (8.5%) of NaClO is added under virurous stirring at 0° C.

TLC shows almost complete conversion. For work up 50 ml of an aqueous sodium thiosulfate solution (10%) is added. Phases are separated and the organic phase is washed with brine, dried over MgSO$_4$ and evaporated to give 0.73 g of a white semi-solid crystalline material which is almost pure product according to NMR and HPLC analysis. The crude material is recrystallised from ethyl acetate/heptane (6 ml/18 ml) to give the pure title compound BOC-lactam-lactone.

The spectroscopic data of the sample are the same as reported in WO 2007/045420 A2, page 64.

Example 15

Benzyloxy protection of (S)-3-Methyl-2-(2-nitro-ethyl)-butan-1-ol

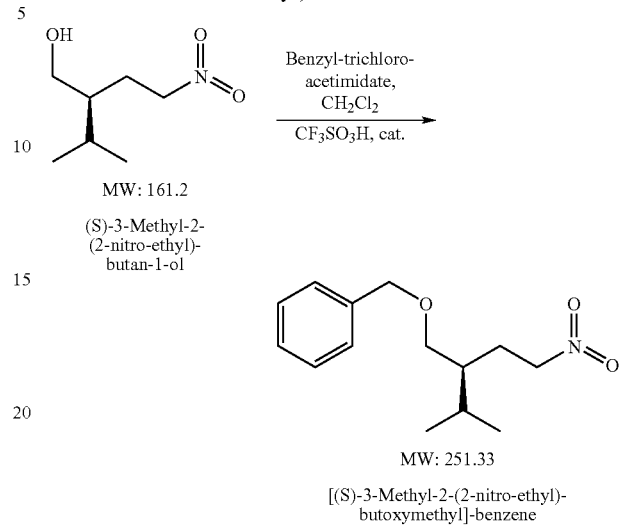

1.0 g (6.2 mmol) of S)-3-Methyl-2-(2-nitro-ethyl)-butan-1-ol is dissolved in 15 ml of dichloromethane at room temperature and 2.35 g (6.8 mmol) of benzyl (2,2,2)-trichloro acetimidate and 50 mg (0.33 mmol) trifluoromethanesulfonic acid as catalyst is added at 0° C. under stirring. A white precipitate of trichloroacetamide is formed after a short periode of time. The reaction mixture is stirred at room temperature over night and after complete conversion (TLC) the reaction mixture is filtered to remove precipitated trichloro acetamide. The filtrate is washed with aqu. saturated bicarbonate solution, with water and dried over Na$_2$SO$_4$. The solvent is evaporated in vacuum to give the crude product. The crude product was chromatographed over silicagel with ethyl acetate/heptane (1:4) to give the product as an oil.

$^1$H-NMR: (400 MHz, CDCl$_3$); $\delta_H$ (ppm) $\delta$=0.83 (6H, d, 2×CH$_3$), 1.43-1.52 (1H, brm, —CH), 1.62-1.72 (1H, m, —CH), 1.88-1.98 (1H, m, —CH), 2.02-2.12 (1H, m, —CH), 3.27-3.33 (1H, dd, —OCH), 3.38-3.44 (1H, dd, —OCH), 4.32-4.48 (4H, comp. m, —CH$_2$—NO$_2$, & —OCH$_2$—Ph), 7.20-7.36 (5H, brm, arom.-H).

MS: [M+H]$^+$=252

IR: (FTIR-Microscopy in transmission) 2961, 2931, 2875, 1552 (—NO$_2$), 1384 (—NO$_2$), 1095 (C—O), 739, 699 [cm$^{-1}$]

Example 16

Nef reaction [(S)-3-Methyl-2-(2-nitro-ethyl)-butoxymethyl]-benzene

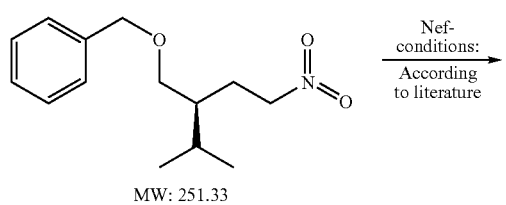

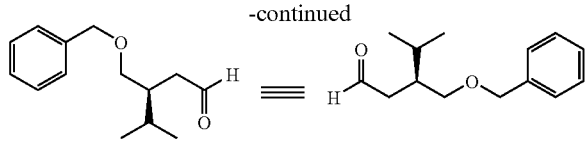

MW: 220.31

[(S)-3-Benzyloxymethyl-
4-methyl-pentanal]

Example 16A

According to Literature Procedure b 1.0 g (4 mmol) of nitro compound from example 15 is dissolved in a mixture of DMF-water (9:1), 10 ml. To this solution is added at room temperature ° C. a solution of commercial sodium percarbonat (5 mmol) in water under stirring. The reaction mixture is warmed up to 40° C. and is stirred until complete conversion (HPLC) of the starting material. The reaction mixture is diluted with water, the pH is adjusted to 7 and the product is extracted from the aqueous phase with ethyl acetate (3×15 ml). The combined organic phases are evaporated in vacuum and the crude product is chromatographed over silica gel with ethyl acetate/heptane (1:4).

The obtained aldehyde is identical by TLC, HPLC and spectroscopic data to the compound obtained in example 11.

Example 16B

According to Literature Procedure d

A solution of 1.0 g (4 mmol) of the nitro compound from example 15 in 10 ml of absol. ethanol is added slowly under stirring to a solution of 640 mg (16 mmol) in 10 ml of ethanol at room temperature and under an $N_2$ atmosphere. After stirring for 15 minutes the ethanol was evaporated in vacuum. The resulting semi-solid sticky sodium nitronate is dissolved in 15 ml of water and the aqueous solution is then added slowly dropwise to a well stirred two layer mixture of sulfuric acid (10%) and n-hexane at 0° C. After complete addition of the sodium nitronate stirring is continued for 1 hour at 0° C. The hexane phase is separated and the aqueous phase was extracted 3-times with n-hexane (25 ml). The combined organic extracts are dried over $MgSO_4$ and then evaporated in vacuum to give crude aldehyde. The crude product was purified by filtration over silicagel with heptane/isopropylacetate (9:1) to give almost pure compound. TLC, HPLC and spectroscopic data are the same as for the compound obtained in example 11.

a) P. Ceccherelli, et al., Synth. Commun., 28, 3054 (1998)

b) G. Kabalka, et al., Synth. Commun., 22, 2587 (1992)

c) F. Urpi, et al., THL, 31, 7499 (1990)

d) H. Chikashita et al., Synth. Commun., 17, 677 (1987)

e) R. Ballini, M. Petrini, Tetrahedron, 60, 1017 (2004), review

The BOC-protected lactam lactone of formula (I) can be further converted to aliskiren as described, e.g. in WO2007/045420. For example, the following methodology can be employed:

Example 17

Reaction of Boc-lactam-lactone with Aryl-Li-compound

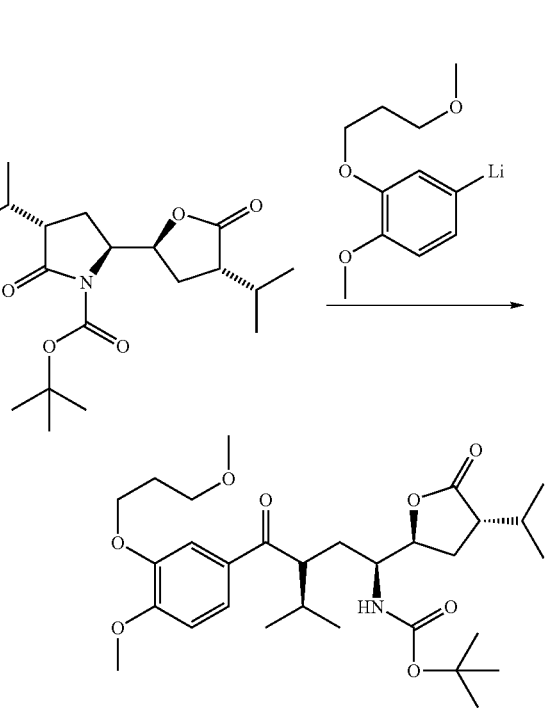

8.56 g (31.12 mmol) aryl bromide are dissolved in 125 ml of THF in a first flask. The solution is cooled at internal temperature of −70° C. To this solution id added over a time of 1 hour 19.8 ml (31.69 mmol) n-butyllithium, 1.6 M solution in hexane. The reaction solution became then a pink-red color. The solution is allowed to stir for 1 hour at −70° C. 10.0 g Boc-lactam-lacton (28.29 mmol) are dissolved in 125 ml of dry THF in a second flask. The solution is cooled at internal temperature-50° C. under a stream of argon. To this solution is added the solution of aryl-lithium compound (from flask N° 1) at −55 to −50° C. over a time of 30 minutes.

The reaction mixture is stirred then at −50° C. over 3 hours. The reaction is cooled to a temperature of −70° C. over night.

The next day a second part of aryl-lithium compound is prepared with 1.28 g aryl bromide (, (4.65 mmol) and 3 ml of n-butyllithium in the same manner as described, and added at internal temperature of −50° C. during a time of 10 minutes to the reaction mixture. The reaction mixture is allowed to stir for 4 hours at −50° C.

For work up the reaction mixture is put on a mixture of 125 ml of toluene and 250 ml of a 10% citric acid solution in water at 0-5° C. during 20 minutes. The quenching is exothermic. The organic phase is washed with 150 ml citric acid, 10% in water, (2×75 ml) and 150 ml $NaHCO_3$ [8%], (2×75 ml). The organic phase is washed to a neutral pH with 150 ml of water (2×75 ml) and evaporated to yield crude compound as a nearly white amorphous solid.

To purify the desired compound a part of the solid (6.72 g, 12.22 mmol) is dissolved in 60 ml of ethanol. To the resulting clear colorless solution are added at 0-5° C. 28 ml of 1N lithium hydroxide solution over a time of 20 minutes. This mixture is allowed to warm up to room temperature (21° C.) and stir at this temperature over a period of 1 hour. After this time water and ethanol is partially evaporated and the resulting precipitate is diluted with 100 ml of water and 50 ml of toluene to give a clear solution. The desired product is now in the basic aqueous phase. The water phase is washed with 150 ml of toluene (3×50 ml). To the water phase is added 75 ml of ethyl acetate. To this reaction mixture 7.1 g (33.66 mmol) of citric acid are added. The protonated product is now in the organic phase. The mixture is allowed to stir at room temperature at the beginning, then later at 50° C. After 12 hours stirring, 3.6 g citric acid (17.1 mmol) are added to the mixture and stirring is continued at 50° C. during 24 h. The water phase is then separated and 7.1 g citric acid in 50 ml of water are added to the organic solution. The biphasic solution is then stirred for additional 6 hours at 50° C. The layers are separated and 7.1 g of citric acid in aqueous solution are added again. The reaction mixture is stirred over night at internal temperature of 50° C. For work up 50 ml of water are added to the reaction solution at room temperature. The organic phase is washed with 50 ml of water (2×25 ml) and 50 ml of NaHCO$_3$ [8%], (2×25 ml). The organic phase is washed to a neutral pH with 50 ml of water (2×25 ml) and evaporated to yield the desired compound as a very viscous oil.

$^1$H-NMR (400 MHz, DMSO-d$_6$): (2 rotamers), 7.52-7.50 (d, 1H), 7.37 (s, 1H), 7.04-7.02 (d, 1H), 6.99 (s, 1H), 4.35-4.31 (m, 1H), 4.06-4.04 (t, 2H), 3.83 (s, 3H), 3.49-3.46 (m, 3H), 3.25 (s, 3H), 2.51-2.49 (m, 1H), 2.05-1.95 (m, 4H), 1.87-1.80 (m, 2H), 1.63-1.58 (t, 1H), 1.25 (s, 9H), 0.97-0.95 (d, 3H), 0.92-0.91 (d, 3H), 0.86-0.84 (d, 3H), 0.83-0.81 (d, 3H), 0.80-0.78 (d, 3H).

MS: [MH-Boc]H$^+$=450
R$_f$=0.45 (heptane:EtOAc=1:1)

Example 18

Direct Hydrogenation of Aryl Carbonyl Compound to Produce {(1S,3S)-1-(S)-4-isopropyl-5-oxotetrahydrofuran-2-yl)-3-[4-methoxy-3-(3-methoxypropoxy)benzyl-4-methylpentyl}carbamic acid tert-butyl ester

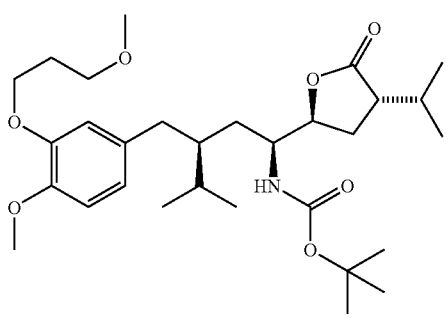

5.5 g (10 mmol) of the aryl carbonyl compound prepared above was dissolved in of a mixture of 90 ml ethanol and 10 ml water. To the mixture is added 5 g of catalyst Pd—C (10%), water cont. ca. 50%, from Johnson Matthey, typ 39. The mixture is stirred at room temperature and normal pressure for 20 hours. After that time the conversion of starting material was 98% and 66% of the desired compound was formed together with 28% of epimeric alcohols and 4% pyrrolidine lactone. Hydrogenation under the same conditions was continued for another 48 hours without additional catalyst. After that time the catalyst was filtered off and the solvent was evaporated under reduced pressure to afford an oil (5.9 g) which contained according to HPLC 89% of the desired product. The oil was treated and stirred at 0° C. with 10 ml of n-heptane (isomer mix) and seeded with a small amount of compound of the desired product upon the product started to crystallize. The flask was stored in the refrigerator over night and for another 24 hours at −18° C. The product was filtered and washed with small volumes of very cold n-heptane to give after drying in vacuum the desired product, which was pure by HPLC, TLC and $^1$H-NMR.

$^1$H-NMR (400 MHz, CDCl$_3$): 0.74-0.76 (2× d, 6H), 0.85-0.87 (d, 3H), 0.92-0.94 (d, 3H), 1.16-1.23 (bm, 1H), 1.38, (s, 9H, Boc), 1.5-1.65 (br-m, 2H), 1.95-2.15 (br-m, 5H), 2.50-2.35 (br-m, 1H), 2.45-2.52 (brm, 1H), 2.50-2.59 (brm, 1H), 3.28 (s, 3H), 3.50 (t, 2H), 3.70-3.80 (s+m, 4H), 4.03 (t, 2H), 4.28-4.35 (m, 2H), 6.62 (d, 1H), 6.67 (s, 1H), 6.69 (d, 1H).

IR: (FTIR-microskop in transmission): 3358 (—NH), 1773 (lactone), 1705 (carbamate), 1518 (amide II) cm$^{-1}$;
MS: MH$^+$=535.7

The above compound can be further reacted with a compound of formula shown below:

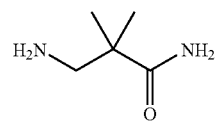

This conversion can proceed according to typical peptide coupling reactions well known in the art, e.g. in analogy to the process disclosed in EP-A-678 503 see in particular examples 124 and 131 or as disclosed in WO 02/02508, in particular example H1 on page 35 (preparation of J1).

The removal of the group BOC is performed using standard protecting group chemistry following the procedures as described in the literature referenced below or using methods well known in the art, see e.g. EP-A-0678 503, in particular example 130, and optionally salt formation using reaction conditions as described e.g. in U.S. Pat. No. 5,559,111, see in particular example 83.

Example 19

4-Benzyloxybutyraldehyde

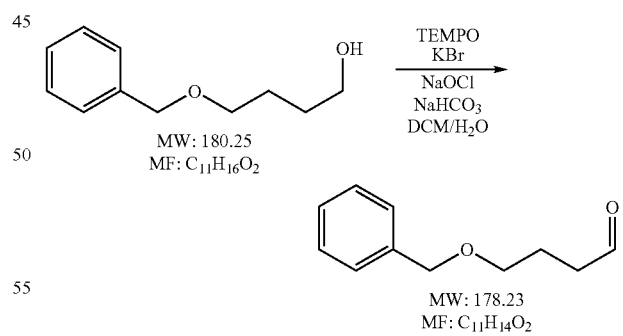

A procedure is followed as described by Rychnovsky (Angew. Chem. Int. Ed. 2004, 43, 2822-2826).

To a stirred solution of 4-benzyloxy-butan-1-ol (50) (10.28 g, 57 mmol) in DCM (570 mL) at 0° C. is added potassium bromide (1.36 g, 11.4 mmol, in water 23 mL), TEMPO (0.178 g, 1.14 mmol) and then a mixture of sodium hypochlorite (9.1% available chlorine, 50 mL, 80 mmol), water (64 mL) and aqueous sodium bicarbonate solution (8%, 114 mL) is added. The orange biphasic mixture is stirred vigorously until the orange colour fades (30 min). The phases are separated and the aqueous layer is extracted with DCM. The combined organics are dried (Na$_2$SO$_4$) and concentrated to yield an orange oil.

$^1$H NMR (400 MHz, CDCl$_3$) δ$_H$ (ppm) 9.80 (1H, s, CHO), 7.38-7.29 (5H, m, Ar—H), 4.50 (2H, s, Ph—CH$_2$O), 3.52 (2H, t, J 6 Hz), 2.56 (2H, dt, J 1.6 Hz, 7.1 Hz), 1.97 (2H, qu, J 7.1 Hz).

Example 20

8-Benzyloxy-5-hydroxy-4-nitrooctanoic acid methyl ester

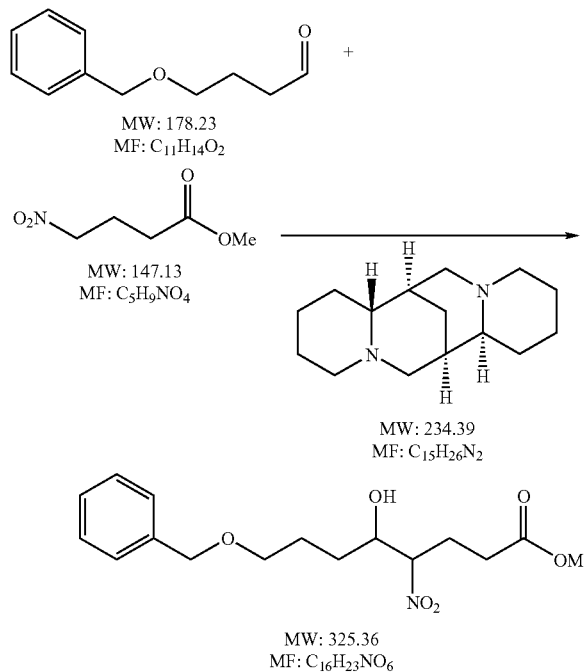

4-benzyloxybutanal (1.463 g, 8.2 mmol), methyl-4-nitrobutyrate (1.29 g, 8.8 mmol) and (−)-sparteine (206 mg, 0.88 mmol) are combined and stirred at RT for 6 hours. EtOAc (5 mL) is added, and the solution is filtered through silica. The solvent is removed in vacuo to yield a pale yellow oil.

$^1$H NMR (600 MHz, DMSO-d$_6$) δ$_H$ (ppm) 7.36-7.26 (5H, m, Ar—H), 5.44/5.40 (1H, d, J 6.7 Hz, OH, syn+anti), 4.59-4.50 (1H, m, CHNO$_2$), 4.45/4.44 (2H, s, Ar—CH$_2$O, syn+anti), 3.91-3.76 (1H, m, CHOH), 3.60 (3H, s, OCH$_3$), 3.44 (2H, t, J 6.1 Hz, OCH$_2$R), 2.43-2.25 (2H, m), 2.21-1.97 (2H, m), 1.83-1.34 (4H, m).

$^{13}$C NMR (150 MHz, DMSO-d$_6$) δ$_C$ (ppm) 172.41/172.10 (C=O), 138.66, 128.24, 127.44, 127.42, 127.36, 92.23/91.13 (CHNO$_2$), 71.78/71.51 (CHOH), 70.80 (ArCH$_2$O), 69.34/69.27 (OCH$_2$R), 51.56/51.50, 29.93/29.83, 29.58/29.53, 25.58, 24.93/24.87.

LRMS (ES+) m/z (ion, intensity) 343 (23, [M+NH$_4$]$^+$), 326 (100, [M+H]$^+$). (ES−) m/z (ion, intensity) 324 (100, [M−H]$^+$).

FTIR v$_{max}$ (neat, cm$^{-1}$) 3435 (br, OH), 3088 (w), 3064 (w), 3031 (w), 2954 (m), 2863 (m), 1737 (s, C=O), 1550 (s, NO$_2$), 1453 (m), 1439 (m), 1365 (m), 1205 (m), 1175 (m), 1098 (m), 741 (m), 700 (m).

Example 21

5-(4-Benzyloxy-1-hydroxy-butyl)pyrrolidin-2-one

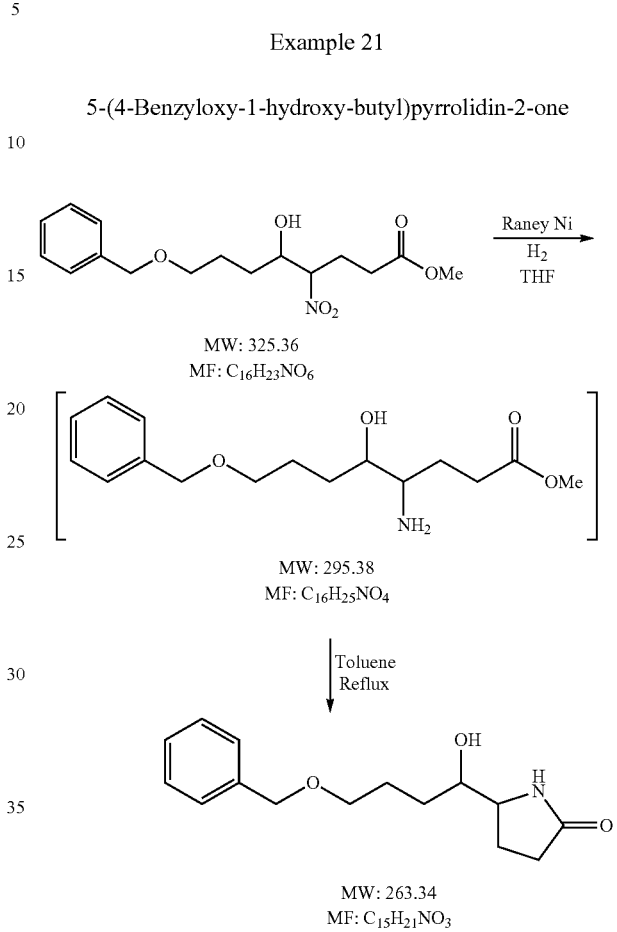

(2.02 g, 6.21 mmol) of ester from the previous experiment (Example 20) in THF (40 mL) is hydrogenated (1 atm, at room temperature) in the presence of Raney-nickel (1 g). Once the reaction is complete, the THF was decanted and the catalyst is washed with THF (3×25 mL). The solvent is removed under vacuum. TLC shows a ninhydrin positive spot indicating that the cyclization is incomplete. The residue is refluxed in toluene (50 mL) for 3 hours. The solvent is removed to yield a brown oil. The residue is dissolved in EtOAc (10 mL) and filtered through silica gel, eluting with EtOAc, then with methanol to elute the product. The solvent is removed to yield the desired product as a brown oil.

$^1$H NMR (600 MHz, DMSO-d$_6$) δ$_H$ (ppm). 7.58+7.50 (1H, s, NH, syn+anti), 7.33-7.25 (5H, m, Ar—H), 4.69 (1H, d, OH), 4.43 (2H, s, OCH$_2$Ar), 3.41 (2H, t, J 6.6 Hz, OCH$_2$R), 3.28 (1H, m, CHNH), 3.21 (1H, m, CHOH), 2.20-1.82 (4H, m, 2× lactam CH$_2$), 1.61-1.14 (4H, m, 2× alkyl CH$_2$).

$^{13}$C NMR (150 MHz, DMSO-d$_6$) δ$_C$ (ppm) 176.95 (C=O), 138.69, 128.10, 127.39, 127.29, 72.94, 71.77, 69.69, 58.34, 30.42, 29.14, 25.69, 21.46.

LRMS (ES+) m/z (ion, intensity) 264 (100, [M+H]$^+$)

FTIR v$_{max}$ (neat, cm$^{-1}$) 3306 (br, OH+NH), 3089 (w), 3064 (w), 3031 (w), 2931 (m), 2861 (m), 1685 (s, C=O), 1496 (w), 1454 (m), 1363 (m), 1276 (br), 1098 (s), 1077 (s), 739 (m), 699 (m).

Example 22

5-(1,4-Dihydroxybutyl)pyrrolidin-2-one

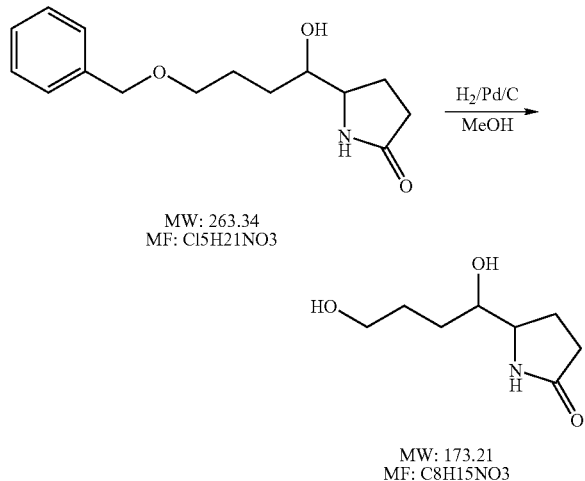

(0.91 g, 3.46 mmol) of benzyloxyether from the previous experiment (Example 21) in MeOH (20 mL) is hydrogenated (1 atm, at room temperature) with palladium on carbon as catalyst (200 mg). Once the reaction is complete, filtration of catalyst is followed by solvent removal under vacuum to yield the desired product.

$^1$H NMR (600 MHz, DMSO-d$_6$) δ$_H$ (ppm) 7.55/7.49 (1H, s, NH, syn+anti), 4.67 (1H, t, J 5.6 Hz, CHOH), 4.39 (1H, q, J 5.3 Hz, CHOH), 3.38 (2H, q, J 6.0 Hz, CH$_2$OH), 3.25-3.20 (1H, m, CHOH), -2.13-1.85 (4H, m), 1.73-1.53 (2H, m), 1.45-1.35 (2H, m), 1.27-1.18 (1H, m).

$^{13}$C NMR (150 MHz, DMSO-d$_6$) δ$_C$ (ppm) 176.91 (C=O), 73.23/71.91 (CHOH), 60.85, 30.18, 29.83, 28.94, 23.01, 21.27.

LRMS (ES+) m/z (ion, intensity) 369 (3, [2M+Na]$^+$), 347 (19, [2M+H]$^+$), 174 (100, [M+H]$^+$), 156 (12, [M−H$_2$O]$^+$).

FTIR ν$_{max}$ (neat, cm$^{-1}$) 3326 (br, OH), 2942 (m), 2877 (m), 1678 (s, C=O), 1442 (m), 1422 (m), 1284 (m), 1059 (m, C—O), 1009 (w).

Example 23

Oxidation to Unsubstituted Lactam-Lactone: 5-(5-Oxotetrahydrofuran-2-yl)pyrrolidin-2-one

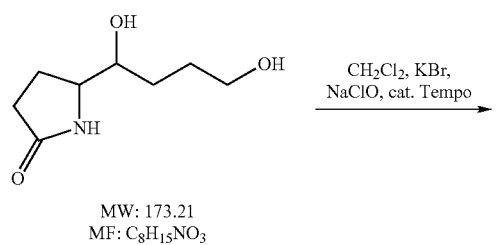

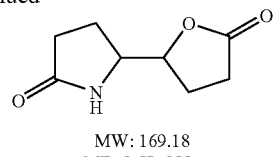

3.0 g (17.3 mmol) of an isomeric mixture of lactam-diol from the previous experiment (Example 22) is dissolved in a biphasic mixture of 52 ml aqueous KHCO3 solution (14%) and 10 ml of a KBr solution (25%), then tempo (0.1 g) in 2 ml of toluene is added. This emulsion is rapidly stirred and cooled to 0-5° C. To this emulsion is added, during 20 min at 0° C. under stirring via dropping funnel, a bleach solution NaClO) (chloro content 8.5% according to titration, 82.3 mmol NaClO, 4.75 equiv.) with respect to starting material. The emulsion is stirred for additional 2 hours. Then, the reaction mixture is quenched with a 10% aqueous thiosulfate solution and stirring is continued for 30 min. The pH is then adjusted to 4 with 6N aqu. HCl. The aqueous phase is then extracted first with ethyl acetate and then with dichloromethane (8×50 ml) to isolate the product from the aqueous phase. The product containing CH$_2$Cl$_2$ extracts are combined and evaporated to give an oil which is treated with diethyl-ether (20 ml) to give white crystals which are filtered off and dried. According to NMR, the crystalline material is a mixture of the two possible stereoisomers, the syn-diastereomer and the anti-diastereomer in a ratio of 1:1. Mp. of the isomer mixture: 130-133° C.

$^1$H NMR (400 MHz, CDCl$_3$), of the diastereomer syn-anti-mixture (1:1) δ$_H$ (ppm) 6.5-6.35 (1H, br.s, NH-amid), 4.52-4.45 (0.5H, br.m, OC—H, syn), 4.42-4.33 (0.5H, q, OC—H, anti), 4.02-3.95 (0.5H, br.m, NC—H, syn), 3.78-3.70 (0.5H, q, NC—H, anti), 2.65-2.55 (2H, m, —CH$_2$), 2.50-2.25 (4H, br.m, —CH$_2$), 2.10-1.80 (2H, br.m, —CH$_2$)

LRMS [M+H]$^+$: 170, MH$^{+-CO=}$142, [2M+H]$^+$=339

FTIR ν$_{max}$ (neat, cm$^{-1}$) 3252 (br, NH), 2940 (m, CH$_{aliph}$), 1773 (s, lactone) 1687 (s, lactam), 1464 (w) 1432 (w), 1289 (m), 1270 (m), 1189 (m, C—O), 1148.

What is claimed is:

1. A process for preparing a compound of formula (V),

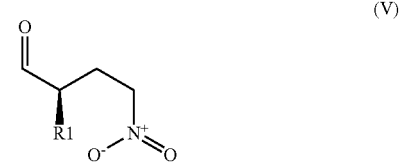

wherein R1 is hydrogen, C$_{1-7}$alkyl, C$_{3-8}$cycloalkyl or benzyl, or a salt thereof, said process comprising an organocatalytic nitro-Michael addition reaction of nitroethylene or a precursor thereof of formula (XII), or salts thereof,

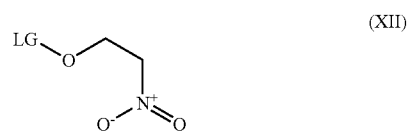

wherein —O-LG is a leaving group that is eliminated under the reaction conditions to reveal nitroethylene, with a compound of formula (IV), or salt thereof,

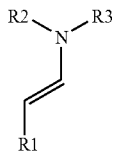
(IV)

wherein
R1 is hydrogen, $C_{1-7}$ alkyl, $C_{3-8}$ cycloalkyl or benzyl;
R2 and R3 together with N form a chiral amine moiety.

2. A process for preparing a compound of formula (VI), or salt thereof,

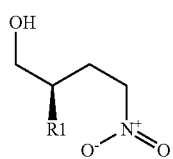
(VI)

wherein R1 is hydrogen, $C_{1-7}$alkyl, $C_{3-8}$cycloalkyl or benzyl, comprising the process of preparation of (V) according to claim 1 and further comprising the reduction of the compound of formula (V) to obtain the compound of formula (VI).

3. The process according to claim 1, wherein, the compound of formula (IV), or salt thereof, is prepared, in situ or in a separate step, by subjecting a compound of formula (II), or a salt thereof,

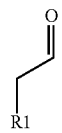
(II)

wherein R1 is hydrogen, $C_{1-7}$alkyl, $C_{3-8}$cycloalkyl or benzyl;
with a chiral amine of formula (III), or salt thereof,

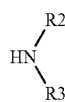
(III)

wherein R2 and R3 are, together with N form a chiral amine moiety.

4. The process according to claim 3, wherein the chiral amine of formula (III), or a salt thereof, is a chiral pyrrolidine derived catalyst suitable for asymmetric Michael reactions.

5. The process according to claim 1, wherein the compound of formula (IV), or salt thereof, is a compound having the formula (IVa), or a salt thereof,

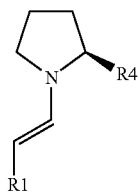
(IVa)

wherein
R4 is carboxy, amido, N (unsubstituted, mono- or di- or substituted $C_{2-7}$alkyl) amido, unsubstituted or substituted $C_{1-7}$alkyl or tetrazolyl;
and R1 is hydrogen, $C_{1-7}$alkyl, $C_{3-8}$cycloalkyl or benzyl.

6. The process according to claim 1, wherein the compound of formula (IV), or salt thereof, is a compound having the formula (IVb), or a salt thereof,

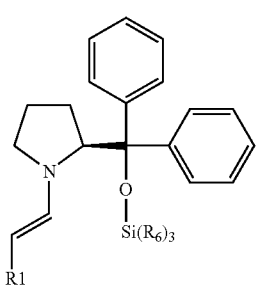
(IVb)

wherein R9 is $C_{1-4}$alkyl or phenyl.

7. The process according to claim 1, wherein R1 is isopropyl.

8. The process according to claim 1, wherein any or all of the steps or all are performed in a continuous flow process.

9. A process for preparing a compound of formula (VII),

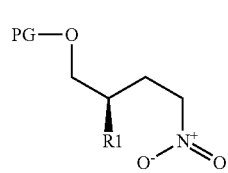
(VII)

wherein R1 is hydrogen, $C_{1-7}$alkyl, $C_{3-8}$cycloalkyl or benzyl and PG is a hydroxyl protecting group, or a salt thereof, said process comprising protecting the hydroxyl functionality of a compound of formula (VI), or salt thereof,

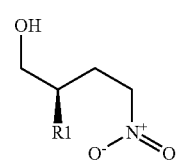
(VI)

wherein R1 is hydrogen, $C_{1-7}$alkyl, $C_{3-8}$cycloalkyl or benzyl, with a protecting group.

10. The process according to claim 9, wherein PG is benzyl.

11. A compound of formula (VII),

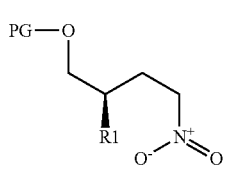

wherein

R1 is isopropyl;

PG is a hydroxyl protecting group;

or a salt thereof.

12. The compound according to claim 11 wherein PG is benzyl.

13. The compound of formula (VIII)

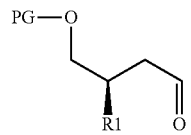

wherein R1 is isopropyl and PG is benzyl.

14. A compound of formula (IX),

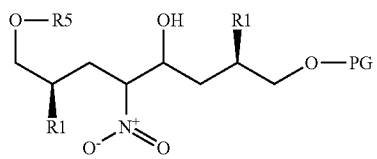

wherein

R1 is isopropyl;

R5 is hydrogen or PG;

PG is a hydroxyl protecting group and whereby both PG's can be the same or different;

or a salt thereof.

15. The compound according to claim 14 wherein PG is benzyl.

16. The compound according to claim 14 having the formula (IXa)

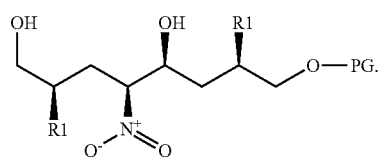

17. A process for preparing a compound of formula (X),

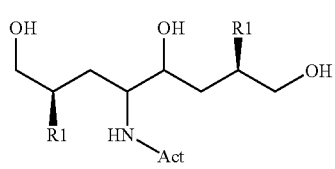

wherein both R1's are the same or different from each other and are hydrogen, $C_{1-7}$alkyl, $C_{3-8}$cycloalkyl or benzyl and Act is an activating group selected from an amino protecting group, in particular one that together with N forms a carbamate, or a salt thereof, said process comprising hydrogenation of the nitro functionality of the compound of formula (IX) according to claim 14 to an amine.

18. The process according to claim 17, comprising as a concomitant or separate step the removal of the protecting group(s) PG to reveal the hydroxyl functionality.

19. The process according to claim 17, comprising as a concomitant or separate step the introduction of the activating group Act on the amine functionality.

20. The process according to claim 17 wherein the compound of formula (X) is obtained in a one-pot synthesis using hydrogenation in the presence of $(Act)_2O$, such as $(Boc)_2O$.

21. A compound of formula (X),

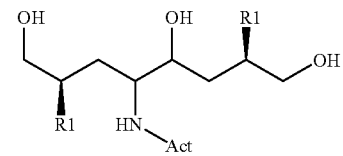

wherein

R1 is isopropyl; and

Act is an activating group selected from an amino protecting group, in particular one that together with N forms a carbamate, or a salt thereof.

22. The compound according to claim 21 wherein R1 is benzyl.

23. The compound according to claim 21 wherein Act is Boc.

24. The compound according to claim 21 having the formula (Xa)

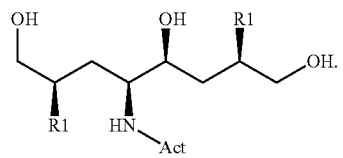

25. A process for preparing a compound of formula (I)

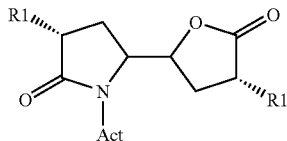

wherein R1 is hydrogen, $C_{1-7}$alkyl, $C_{3-8}$cycloalkyl or benzyl and Act is as defined for a compound of formula (X), or a salt thereof, said process comprising selective oxidation of the primary alcohols of the compound of formula (X) according to claim 21 to effect double ring closure into to the lactone lactam.

26. A process for preparing a compound of formula (VIII),

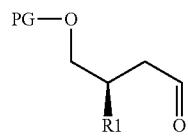

wherein R1 is hydrogen, $C_{1-7}$alkyl, $C_{3-8}$cycloalkyl or benzyl and PG is as defined for a compound of formula (VII), or a salt thereof, said process comprising reduction of the nitrile functionality of a compound of formula (XIV),

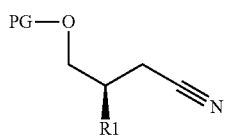

wherein R1 is hydrogen, $C_{1-7}$alkyl, $C_{3-8}$cycloalkyl or benzyl, and PG is as defined for a compound of formula (VII), or a salt thereof, into an aldehyde functionality.

27. A process for preparing a compound of formula (XVI),

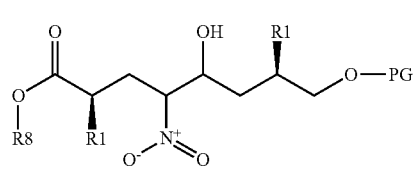

wherein both R1s are the same or different from each other and are hydrogen, $C_{1-7}$alkyl, $C_{3-8}$cycloalkyl or benzyl, R8 is $C_{1-7}$alkyl, and PG is as defined for a compound of formula (VII), or a salt thereof, said process comprising a nitro-aldol (Henry) reaction of a nitro compound of formula (XV)

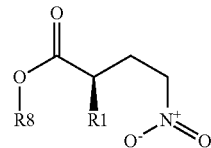

wherein R8 is $C_{1-7}$alkyl, R1 is hydrogen, $C_{1-7}$alkyl, $C_{3-8}$cycloalkyl or benzyl, and PG is a hydroxyl protecting group, or a salt thereof, together with the aldehyde of formula (VIII) according to claim 26.

28. A compound of the formula (XVI)

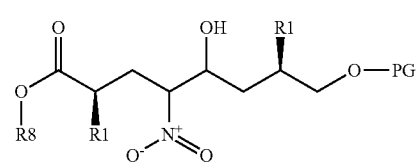

wherein
both R1's are the same or different from each other and are hydrogen, $C_{1-7}$alkyl;
R8 is $C_{1-7}$alkyl;
PG is a hydroxyl protecting group;
or a salt thereof.

29. A process for preparing a compound of formula (XVII),

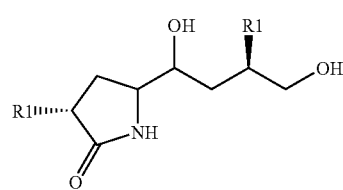

wherein both R1's are the same or different from each other and are hydrogen, $C_{1-7}$alkyl, $C_{3-8}$cycloalkyl or benzyl, or a salt thereof, said process comprising hydrogenation of the nitro functionality of the compound of formula (XVI) according to claim 28 to effect ring closure to form the lactam.

30. The process according to claim 29, comprising as a concomitant or separate step the removal of the protecting group PG to reveal the hydroxyl functionality.

31. A compound of the formula (XVII)

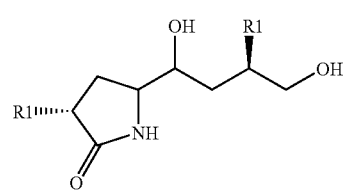

wherein
both R1's are the same or different from each other and are hydrogen, $C_{1-7}$alkyl, $C_{3-8}$cycloalkyl or benzyl;
or a salt thereof.

32. A process for preparing a compound of formula (XVIII),

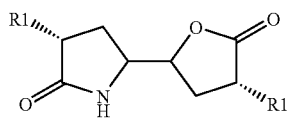

wherein each R1 is, independently of each other, hydrogen, $C_{1-7}$alkyl, $C_{3-8}$cycloalkyl or benzyl, or a salt thereof, said process comprising selective oxidation of the primary alcohol of the compound of formula (XVII) according to claim 31 to effect ring closure to the lactone lactam.

33. A compound of formula (I), or salt thereof, having one of the following structures:

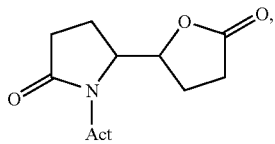

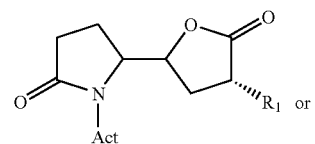

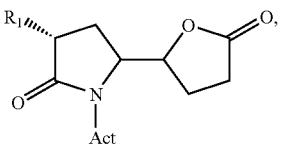

wherein R1 is hydrogen, $C_{1-7}$alkyl, $C_{3-8}$cycloalkyl or benzyl and Act is an activating group selected from an amino protecting group, in particular one that together with N forms a carbamate.

34. A compound of formula (I) according to claim 33, having one of the following structures:

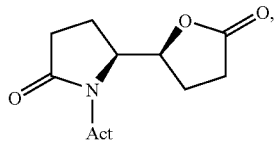

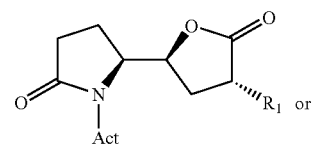

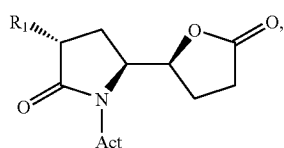

wherein R1 is hydrogen, $C_{1-7}$alkyl, $C_{3-8}$cycloalkyl or benzyl and Act is an activating group selected from an amino protecting group, in particular one that together with N forms a carbamate.

35. A compound of formula (I), or salt thereof, having one of the following structures:

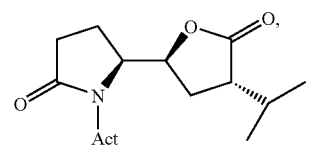

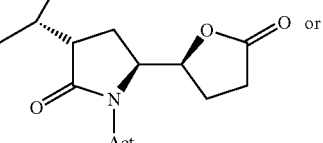

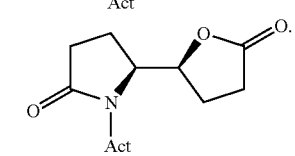

wherein Act is an activating group selected from an amino protecting group, in particular one that together with N forms a carbamate.

36. A compound of formula (V),

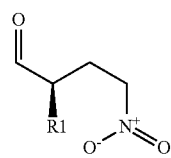

wherein
R1 is isopropyl or a salt thereof.

37. A compound of formula (VI),

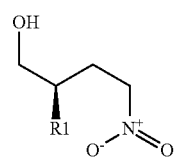

wherein
R1 is isopropyl
or a salt thereof.

38. A compound of formula (XVIII)
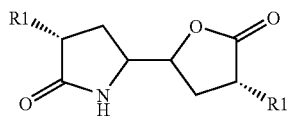
(XVIII)
having one of the following structures:
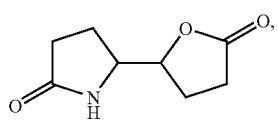
(XVIIIA)
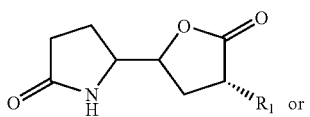
(XVIIIC)
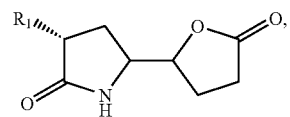
(XVIIID)
wherein R1 is hydrogen, $C_{1-7}$alkyl, $C_{3-8}$cycloalkyl or benzyl.
39. A compound of formula (XVIII) according to claim 38, having one of the following structures:
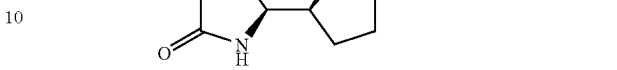
(XVIIIB)
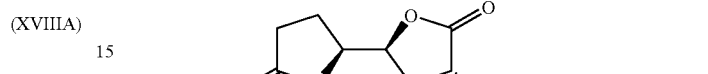
(XVIIIE)
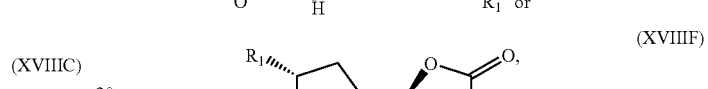
(XVIIIF)
wherein R1 is hydrogen, $C_{1-7}$alkyl, $C_{3-8}$cycloalkyl or benzyl.
* * * * *